(12) United States Patent
Augustyn et al.

(10) Patent No.: US 8,161,968 B2
(45) Date of Patent: Apr. 24, 2012

(54) MEDICAMENT DISPENSER

(75) Inventors: Stephen Augustyn, Milton Keynes (GB); Michael Birsha Davies, Ware (GB); Stephen James Harvey, Ware (GB); Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1294 days.

(21) Appl. No.: 10/565,515

(22) PCT Filed: Jul. 21, 2004

(86) PCT No.: PCT/EP2004/008235
§ 371 (c)(1),
(2), (4) Date: Jan. 23, 2006

(87) PCT Pub. No.: WO2005/014089
PCT Pub. Date: Feb. 17, 2005

(65) Prior Publication Data
US 2006/0196504 A1 Sep. 7, 2006

(30) Foreign Application Priority Data

Jul. 24, 2003 (GB) .................... 0317374.7

(51) Int. Cl.
*A61M 16/00* (2006.01)
(52) U.S. Cl. .............. 128/203.15; 128/203.21
(58) Field of Classification Search ........... 128/203.14, 128/203.15, 203.21
See application file for complete search history.

(56) References Cited

U.S. PATENT DOCUMENTS

| | | | |
|---|---|---|---|
| 3,269,389 A | 8/1966 | Meurer et al. | |
| 4,735,358 A * | 4/1988 | Morita et al. | 239/1 |
| 4,811,731 A | 3/1989 | Newell et al. | |
| 4,860,419 A * | 8/1989 | Hekman | 29/888.09 |
| 4,940,966 A | 7/1990 | Pettigrew et al. | |
| 5,002,048 A | 3/1991 | Makiej, Jr. | |
| 5,007,419 A | 4/1991 | Weinstein et al. | |

(Continued)

FOREIGN PATENT DOCUMENTS

DE 1461280 2/1969

(Continued)

OTHER PUBLICATIONS

U.S. Appl. No. 11/996,762 filed Jan. 25, 2008.

*Primary Examiner* — Clinton T Ostrup
(74) *Attorney, Agent, or Firm* — Robert J. Smith

(57) ABSTRACT

There is provided a medicament dispenser for containing plural elongate form medicament carriers, each having multiple distinct medicament dose portions carried thereby, the dispenser having a housing of generally non-circular form, and within said housing a dispensing mechanism for dispensing the distinct medicament dose portions carried by each of said plural medicament carriers. The mechanism comprises at least one receiving station for receiving each of the plural medicament carriers; a release for releasing in combination a distinct medicament dose portion from each of the plural medicament carriers on receipt thereof by said receiving station; an outlet, positioned to be in communication with the distinct medicament dose portions releasable by said release; and at least one indexer for individually indexing the distinct medicament dose portions of each of the plural medicament carriers. The dispenser contains plural elongate form medicament carriers, each having multiple distinct dose portions carried thereby. At least one of said medicament carriers has the form of a continuous loop.

16 Claims, 19 Drawing Sheets

U.S. PATENT DOCUMENTS

| | | | |
|---|---|---|---|
| 5,320,095 A | 6/1994 | Nijkerk et al. | |
| 5,437,267 A | 8/1995 | Weinstein et al. | |
| 5,462,205 A | 10/1995 | Keller | |
| 5,497,765 A | 3/1996 | Praud et al. | |
| 5,505,704 A | 4/1996 | Pawelka et al. | |
| 5,590,645 A | 1/1997 | Davies et al. | |
| 5,619,984 A * | 4/1997 | Hodson et al. | 128/203.15 |
| 5,664,557 A | 9/1997 | Makiej, Jr. | |
| 5,740,793 A * | 4/1998 | Hodson et al. | 128/203.15 |
| 5,772,085 A | 6/1998 | Bryant et al. | |
| 5,787,881 A | 8/1998 | Chawla | |
| 5,830,490 A | 11/1998 | Weinstein et al. | |
| 5,860,419 A | 1/1999 | Davies et al. | |
| 5,873,360 A | 2/1999 | Davies et al. | |
| 5,921,237 A * | 7/1999 | Eisele et al. | 128/203.21 |
| 5,941,241 A | 8/1999 | Weinstein et al. | |
| 6,029,663 A | 2/2000 | Cameron et al. | |
| 6,102,179 A | 8/2000 | Hodson | |
| 6,116,237 A | 9/2000 | Hill et al. | |
| 6,182,655 B1 | 2/2001 | Keller et al. | |
| 6,810,873 B1 | 11/2004 | Haikarainen et al. | |
| 6,889,690 B2 * | 5/2005 | Crowder et al. | 128/203.15 |
| 2001/0027789 A1 | 10/2001 | Goede et al. | |
| 2002/0040713 A1 | 4/2002 | Eisele et al. | |
| 2004/0050864 A1 | 3/2004 | Stradella | |
| 2005/0126568 A1 | 6/2005 | Davies et al. | |
| 2005/0154491 A1 | 7/2005 | Anderson et al. | |
| 2005/0172964 A1 * | 8/2005 | Anderson et al. | 128/203.21 |
| 2006/0196504 A1 | 9/2006 | Augustyn et al. | |

FOREIGN PATENT DOCUMENTS

| | | |
|---|---|---|
| EP | 0469814 | 2/1992 |
| EP | 0521434 | 1/1993 |
| EP | 0751077 | 1/1997 |
| EP | 1300171 | 4/2003 |
| GB | 1387954 | 3/1975 |
| GB | 2242134 | 9/1991 |
| GB | 2327408 | 1/1999 |
| WO | 9212402 | 7/1992 |
| WO | 9631790 | 10/1996 |
| WO | 9830332 | 7/1998 |
| WO | 9834664 | 8/1998 |
| WO | 9851257 | 11/1998 |
| WO | 9939991 | 8/1999 |
| WO | 0000411 | 1/2000 |
| WO | 0045879 | 8/2000 |
| WO | 0064519 | 11/2000 |
| WO | 0064520 | 11/2000 |
| WO | WO 0064519 A1 * | 11/2000 |
| WO | WO 0064520 A1 * | 11/2000 |
| WO | 0104118 | 1/2001 |
| WO | 0117595 | 3/2001 |
| WO | WO 0117595 A1 * | 3/2001 |
| WO | 0124690 | 4/2001 |
| WO | 0126020 | 4/2001 |
| WO | 0126021 | 4/2001 |
| WO | 0126720 | 4/2001 |
| WO | 0139823 | 6/2001 |
| WO | 0141849 | 6/2001 |
| WO | 0168169 | 9/2001 |
| WO | WO 0168169 A1 * | 9/2001 |
| WO | 0198176 | 12/2001 |
| WO | WO 0197886 A1 * | 12/2001 |
| WO | 0200279 | 1/2002 |
| WO | 0204055 | 1/2002 |
| WO | 0224268 | 3/2002 |
| WO | 02053294 | 7/2002 |
| WO | 03024514 | 3/2003 |
| WO | WO 03024514 A1 * | 3/2003 |
| WO | 03061743 | 7/2003 |
| WO | 03080149 | 10/2003 |
| WO | 03090825 | 11/2003 |
| WO | 03095010 | 11/2003 |
| WO | 04011070 | 2/2004 |
| WO | 04012801 | 2/2004 |
| WO | 04054646 | 7/2004 |
| WO | 05014089 | 2/2005 |
| WO | 05037353 | 4/2005 |
| WO | 005079727 | 9/2005 |
| WO | 06018261 | 2/2006 |
| WO | 07012871 | 2/2007 |

* cited by examiner

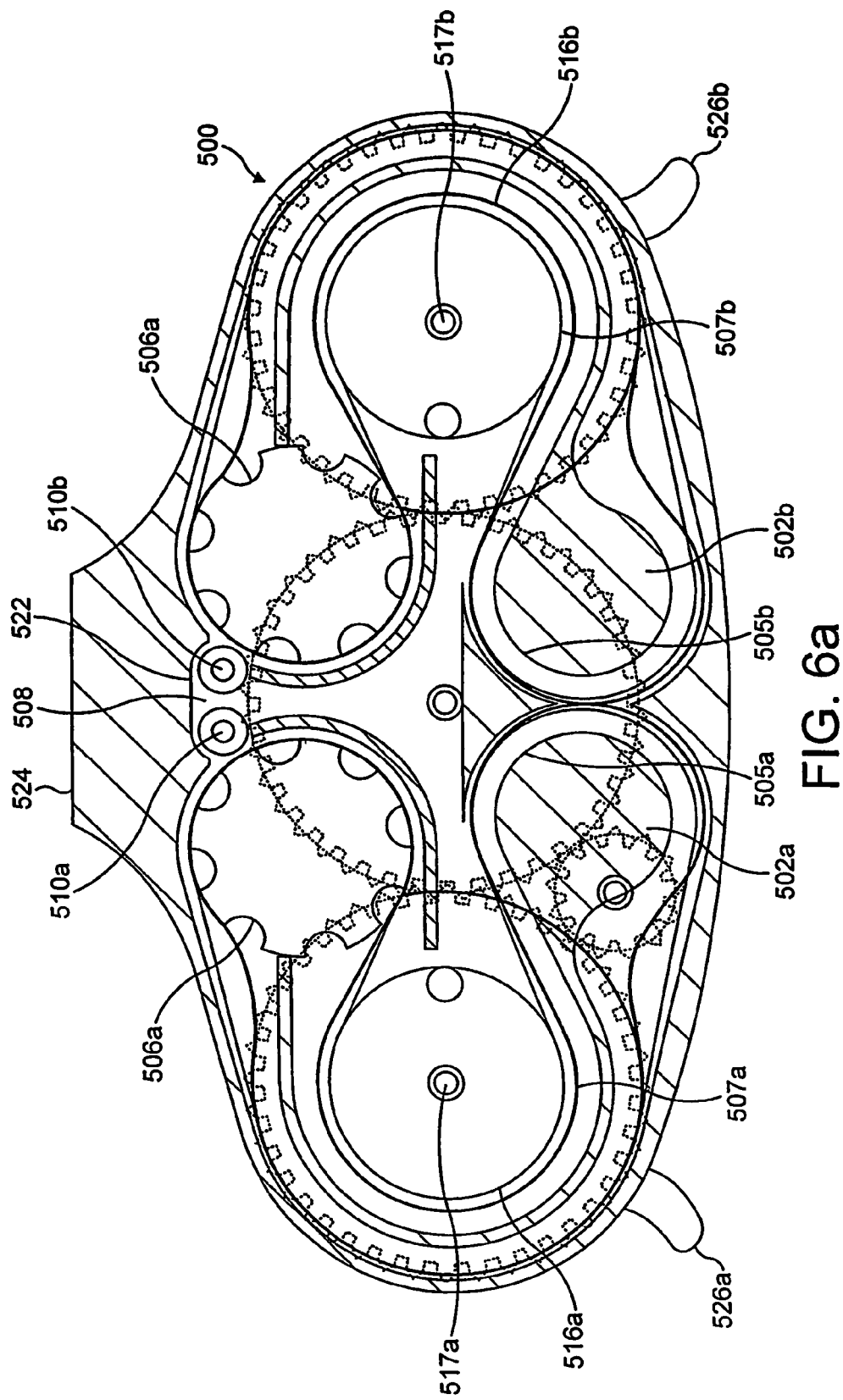

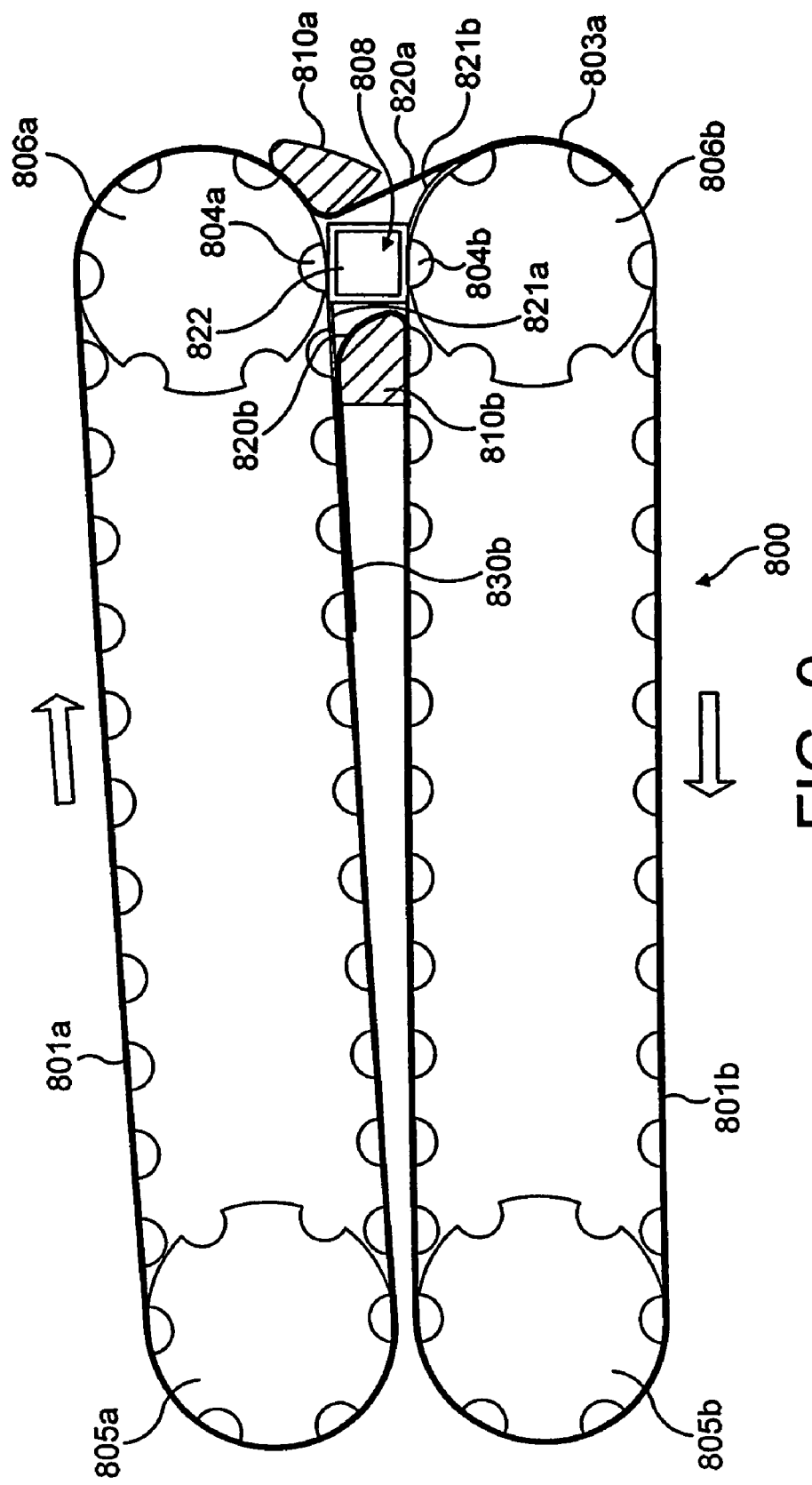

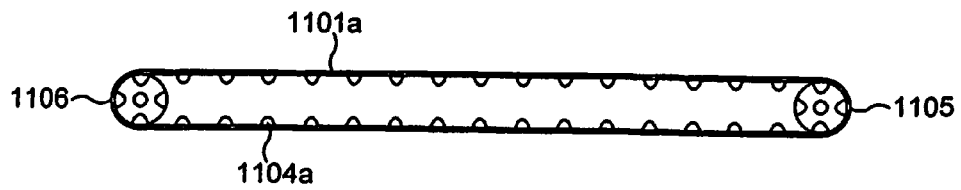
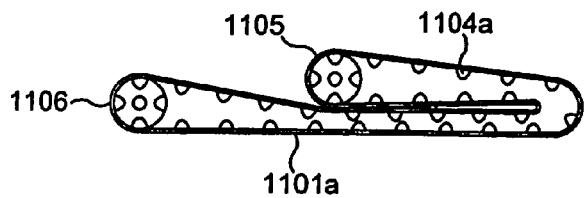
FIG. 12a
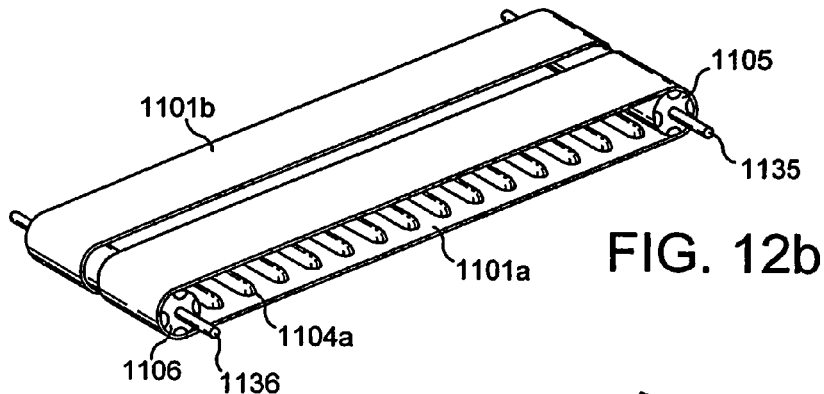
FIG. 12b
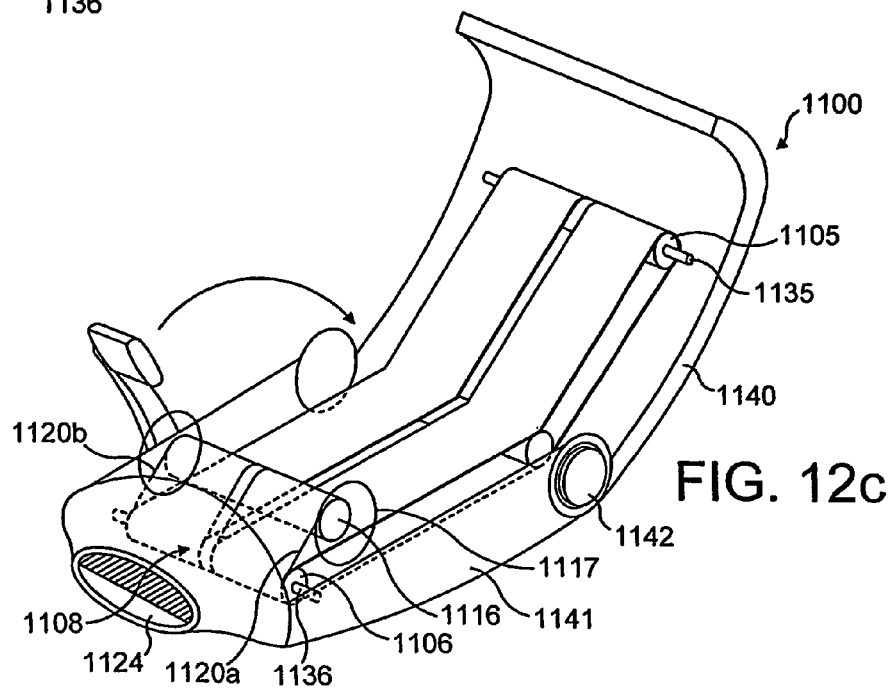
FIG. 12c

MEDICAMENT DISPENSER

CROSS-REFERENCE TO RELATED APPLICATIONS

This application is filed pursuant to 35 U.S.C. §371 as a United States National Phase Application of International Application No. PCT/EP2004/008235 filed 21 Jul. 2004, which claims priority from GB 0317374.7 filed 24 Jul. 2003.

TECHNICAL FIELD

The present invention relates to a medicament dispenser for dispensing medicament. The invention particularly relates to a dispenser for use in dispensing medicament in powder or tablet form.

BACKGROUND OF THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism of accessing these doses, usually comprising either piercing means or means to peel a lid sheet away from a base sheet. The powdered medicament can then be accessed and inhaled. Such a mechanism may also be used for dispensing medicament in tablet form wherein peeling away the lid sheet from the base sheet reveals a tablet for removal and subsequent consumption.

Therapies involving combinations of different and complementary active medicaments are known. These can be administered either as distinct combination (i.e. multi-active) medicament products, which comprise a defined mixture of each component medicament, or as groups of single active medicament products, which are designed to be taken in combination or sequentially. Whilst combination products offer added convenience for the patient, certain medicament actives are difficult to formulate as distinct combination products. For example, the actives may interact chemically with each other in an undesirable way when formulated together.

It is thus, desirable in certain circumstances, to have a medicament dispenser that separately (i.e. in isolated fashion) contains each active component (or mixture thereof) of a combination product, but which enables the delivery of a combined dose in response to a minimum number of patient actions. In particular, it is desirable that all active components of the combined dose are delivered to the patient in a single, combined dose in response to a single patient dosing action. For example, it is desirable that a combination inhaled medicament product be delivered in response to a single actuation of an inhaler, even where the active components of that combined product are separately stored within the inhaler device.

A particularly effective way to meet the above described desiderata is provided by a medicament dispenser which comprises plural, separate elongate form medicament carriers (e.g. strip or continuous loop form blister packs), each containing in isolated fashion, a different medicament active (or mixture thereof), wherein the dispenser enables release of the medicament actives from each separate blister pack to provide a combined dose for administration to a patient.

Such a medicament dispenser for use with plural elongate form medicament carriers, each having multiple distinct medicament dose portions carried thereby, typically comprises a dispensing mechanism for sequentially dispensing the distinct medicament dose portions carried by each of said plural medicament carriers. The dispensing mechanism suitably comprises a receiving station for receiving each of the plural medicament carriers; a release for releasing a distinct medicament dose portion from each of the plural medicament carriers on receipt thereof by said receiving station; an outlet, positioned to be in communication with the distinct medicament dose portions releasable by said release; and an indexer for individually indexing the distinct medicament dose portions of each of the plural medicament carriers. A medicament dispenser of this type has been described in Applicant's previous PCT application no. WO 03/061743.

The Applicant has now found that in providing a medicament dispenser of this type a number of practical problems and design challenges are encountered.

One problem is that of providing a dispenser device that is able to accommodate the plural medicament carriers, but is of sufficiently small overall size that it is conveniently portable (e.g. in the pocket or bag of a patient) and amenable to discrete use, by the patient. Herein, the Applicant describes a number of ways to ameliorate the problem of 'saving space' within the dispenser including the use of medicament carriers in continuous loop form housed within a non-circular form housing.

Another problem is that of providing a dispenser device, in which the distinct medicament dose portions of each of the plural medicament carriers may be indexed or accessed without the need for the user to apply undue indexing or accessing force. Particular challenges are faced when the plural medicament carriers are required to be moved through the dispenser device for indexing/accessing thereof, and where the indexing/accessing action is coupled (e.g. moving peelable blister strips through the dispenser device to both index a particular blister on each strip and peelably access that blister). The Applicant herein describes a number of ways to ameliorate the problem of 'reducing user force' required for actuation.

Another problem is that of providing a dispenser device that is able to accommodate the plural medicament carriers and enable efficient indexing/accessing, but which may be configured in an overall form that is ergonomically suitable for patient usage.

Another problem is that of providing a dispenser device that is readily actuable by a conveniently located actuation lever.

Various additional and subsidiary problems are also described herein, and means for addressing them also described.

SUMMARY OF THE INVENTION

According to one aspect of the present invention there is provided a medicament dispenser for containing plural elongate form medicament carriers, each having multiple distinct medicament dose portions carried thereby, said dispenser having a housing of generally non-circular form, and within said housing a dispensing mechanism for dispensing the distinct medicament dose portions carried by each of said plural medicament carriers, said mechanism comprising, a) at least one receiving station for receiving each of the plural medicament carriers;

b) a release for releasing in combination a distinct medicament dose portion from each of the plural medicament carriers on receipt thereof by said receiving station;

c) an outlet, positioned to be in communication with the distinct medicament dose portions releasable by said release; and d) at least one indexer for individually indexing the distinct medicament dose portions of each of the plural medicament carriers, wherein said dispenser contains plural elongate form medicament carriers, each having multiple distinct dose portions carried thereby and at least one of said medicament carriers has the form of a continuous loop.

In one aspect, all of the medicament carriers have the form of a continuous loop.

The housing of the dispenser suitably defines a shell for enclosing the dispensing mechanism and medicament carriers. The housing is of generally non-circular form.

Suitably, the housing has an elongate form. In one aspect, the housing defines a generally ovoid profile (i.e. it has an ovular form), which may be a flat ovoid.

In one aspect, the housing is arranged to be foldable about an axis. Suitably, the housing is hinged about a conventional or 'living hinge' to facilitate such folding. In the folded form, the housing is generally more compact such as to facilitate carrying of the dispenser in the pocket of a user.

The plural elongate form medicament carriers may adopt essentially suitable profile within the dispenser. Preferably, the housing is shaped such as to define a profile that facilitates space-efficient arrangement of the carriers within the housing.

In one aspect, at least one of the plural elongate form medicament carriers adopts a C-shaped profile. In another aspect, at least one of the plural elongate form medicament carriers adopts an S-shaped profile. In a further aspect, at least one of the plural elongate form medicament carriers adopts a caterpillar track profile (e.g. like the caterpillar track on a military tank vehicle).

In combination, the distinct medicament dose portions releasable from each of the plural medicament carriers comprise a defined dose of combination product. That is to say, that when combined together (e.g. on release) the distinct active medicament dose portions form a single dose of a 'multi-active' medicament treatment.

The medicament dispenser is designed to receive plural elongate form medicament carriers. Preferably, the medicament dispenser is designed to receive from two to four such elongate form medicament carriers, more preferably two such carriers. For flexibility it is also envisaged that the medicament dispenser may be used with only one medicament carrier, the other parts of the dispenser mechanism being essentially redundant in this usage pattern.

Each medicament carrier has multiple distinct dose portions carried thereby. The distinct dose portions are typically arranged in spaced fashion, more preferably in progressive arrangement (e.g. series progression) on the carrier such that each dose portion is separately accessible.

The term medicament carrier herein is used to define any suitable form of carrier. Suitably, each elongate form medicament carrier is in the form of a strip or tape, which may either have open ends or ends joined up such as to form a continuous loop. In one preferred aspect, the carrier has a blister pack form, but it could also, for example, comprise a carrier onto which medicament has been applied by any suitable process including printing, painting and vacuum occlusion.

In one aspect, the medicament carrier comprises a blister pack in laminate form. Suitably, the laminate comprises material selected from the group consisting of metal foil, organic polymeric material and paper. Suitable metal foils include aluminium or tin foil having a thickness of from 5 to 100 μm, preferably from 10 to 50 μm, such as 20 to 30 μm.

Suitable organic polymeric materials include polyethylene, polypropylene, polyvinyl chloride and polyethylene terephthalate.

Access to the medicament dose portions comprised within the pockets of the elongate strip form carrier is by any suitable access means including tearing, piercing or peeling apart the relevant pockets.

One suitable blister pack form medicament carrier comprises a peelable blister strip. Suitably, the peelable blister strip comprises a base sheet in which blisters are formed to define pockets therein for containing distinct medicament dose portions and a lid sheet which is hermetically sealed to the base sheet except in the region of the blisters in such a manner that the lid sheet and the base sheet can be peeled apart. The base and lid sheets are typically sealed to one another over their whole width except for the forward end portions where they are typically not sealed to one another at all. Thus, separate base and lid sheet forward end portions are presented at the end of the strip. The respective base and lid sheets are peelably separable from each other to (e.g. separately) release the contents of each pocket.

Suitably, the lid sheet comprises at least the following successive layers: (a) paper; adhesively bonded to (b) polyester; adhesively bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

Suitably, the base sheet comprises at least the following successive layers: (a) oriented polyamide (OPA); adhesively bonded to (b) aluminium foil; adhesively bonded to (c) a third layer comprising a polymeric material (e.g. polyvinyl chloride).

Various known techniques can be employed to join the lid and base sheet and hence to seal the blisters of the peelable blister strip. Such methods include adhesive bonding, hot metal bonding, hot metal welding, radio frequency welding, laser welding, ultrasonic welding and hot bar sealing. The lid sheet and base sheet of the peelable blister strip are particularly sealable by 'cold form' sealing methods, which are conducted at lower temperatures than conventional heat sealing methods. Such 'cold form' sealing methods are of particular utility where the medicament or medicament formulation for containment within the blister is heat sensitive (e.g. degrades or denatures on heating). Suitable 'cold form' sealing methods are conducted at a temperature in the range of 150-250° C., more preferably, 210-240° C.

Each medicament carrier has multiple distinct (i.e. separate) medicament dose portions carried thereby. The term 'dose portion' is employed because in the context of the invention the distinct 'portions' are brought together to form a combination (i.e. multi-active) product dose. in one aspect, each 'dose portion' comprises a single active (i.e. monoactive) medicament component. Each mono-active component is therefore brought together only at the time of release to form the overall combination product.

In another aspect, one or more of the 'dose portions' comprise plural active medicament components (e.g. as a formulated mixture thereof). Typically, these plural components will be 'co-formulation compatible' wherein that term is used to mean compatible in the sense of being amenable to co-formulation, perhaps even displaying synergetic co-formulation characteristics.

In one particular aspect, a first elongate form medicament carrier has multiple distinct mono-active medicament dose portions carried thereby and a second elongate form medicament carrier has multiple distinct plural-active (particularly, bi-active dose portions i.e. comprising two active components) medicament dose portions carried thereby. In combination, the mono-active and plural-active medicament components comprise a defined combination product. That is to say, that when combined together the distinct mono- and bi-active medicament dose portions released by actuation of the dispenser form a dose of a 'multi-active' medicament treatment.

In one aspect, each of the elongate form medicament carriers is sized and shaped to carry equivalent dose portions, that is to say each carrier is suitable for carrying dose portions of equivalent dose volume or dose weight. In one particular example, each medicament carrier of a bi-carrier dispenser is arranged to carry plural 12 mg (or 25 mg) dose portions.

In another aspect, each of the elongate form medicament carriers is sized and shaped to carry non-equivalent dose portions, that is to say each carrier is arranged to carry dose portions of non-equivalent dose volume or dose weight to the other. In one specific example, a first medicament carrier of a bi-carrier dispenser is arranged to carry plural 12 mg dose portions and the second carrier thereof is arranged to carry 25 mg dose portions.

In one aspect, the multiple distinct dose portions are provided to each carrier in uniform series. In particular, the spacing (i.e. pitch) between each dose portion is uniform throughout the series. In other aspects however, the spacing (i.e. pitch) may vary throughout the series (i.e. be non-uniform). In specific examples, the pitch may progressively decrease or progressively increase throughout the series. Such variation may in aspects, be required to compensate for non-uniform indexing by the carrier indexing and/or advancement mechanism of a particular dispenser.

In one aspect, the spacing (i.e. pitch) between each dose portion is equivalent for each carrier of the dispenser. That is to say, each medicament carrier is equivalently pitched. In other aspects, the spacing between each dose portion is non-equivalent for each carrier of the dispenser. Such variation of the spacing (i.e. pitch) from carrier to carrier can be used to enable flexibility in (combination) dosage patterns.

In one particular example, the spacing (i.e. pitch) of a first carrier is arranged to be half that of a second carrier. This arrangement is beneficially employed where the dose interval (i.e. time between doses) of the medicament carried by the first carrier is twice that of the medicament carrier by the second carrier (e.g. in a twice daily/once daily type dosage regime).

The plural elongate form medicament carriers may be provided to the dispenser in any suitable configuration. One suitable configuration is the 'side-by-side' configuration, in which for example, two carriers (e.g. two coiled blister strips) are arranged to lie in sideways alignment with each other in the dispenser. Another suitable configuration is the 'double-decker' configuration, in which for example, two carriers (e.g. two coiled blister strips sharing the same coiling axis) are arranged to lay one on top of each other in the dispenser.

The plural carriers are typically provided to the dispenser as separate entities. Alternative embodiments are however, envisaged in which the separate plural elongate carriers are joined together in some appropriate fashion. Thus, for example in a variation of an embodiment comprising two separate elongate strip form carriers each carrying multiple distinct medicament dose portions arranged in series along the respective strip and mountable in the dispenser in 'double-decker' configuration there might be provided a single strip comprising two separate series of multiple distinct medicament dose portions arranged in 'double decker' configuration (i.e. parallel to each other) as if the two strips of the first embodiment had simply been joined together along adjoining elongate sides thereof.

In a particular 'joined together' configuration, two elongate strip form carriers are arranged in 'back-to-back' configuration (i.e. one strip backs onto the other with the pockets of each facing outwards). In this embodiment, the 'back-to-back' conjoined strip typically has pockets arranged to alternate—one on its first side, then one on the other side. It will be appreciated that when so joined together, each component foil strip of the conjoined whole effectively acts as a 'lid foil' for the other.

In one aspect, the elongate form carrier is arranged to have a continuous loop form such as may be achieved by joining the lead end of the strip to the tail end. All suitable methods of joining are envisaged, including adhesive bonding, hot metal bonding, hot metal welding, radio frequency welding, laser welding, ultrasonic welding and hot bar sealing. The loop may be linearly formed or it may be formed as a Mobius strip.

In a particular aspect where the elongate form carrier is in the form of a peelable strip, the base sheet is formed as a continuous loop. In variations, the lid sheet, which forms a peelable sealing lid to the base sheet, may either have continuous loop or non-continuous loop form.

Hybrid configurations are also envisaged, in which one or more elongate carriers are in the form of an open strip (i.e. with unjoined ends) and one or more further elongate carriers is in the form of a continuous loop (e.g. formed by joining together the lead and tail ends of an open strip).

The dispenser has a dispensing mechanism for dispensing the distinct medicament dose portions carried by each of said plural medicament carriers for administration as a single, combination product dose by the patient.

In aspects, some or all components of the dispensing mechanism are common for each of the medicament carriers. The advantage of having common components is that the number of separate parts in the dispenser may be reduced.

In other aspects, the action of those components that are not common may in aspects be suitably coupled. Coupling is achieved by any suitable fashion including mechanical linkages (e.g. co-gearing or via the use of coupling arms/rods) or electromechanical coupling controls. The advantage of coupling is that the indexing/advancement of each medicament carrier may be achieved in coupled fashion.

In other aspects, most or even all of the components of the dispensing mechanism are distinct. In one particular aspect, the dispenser is arranged such that each of the plural medicament carriers can be indexed/advanced separately thereby providing the opportunity for complex dosing patterns in which any combination, or indeed any one, of the plural strips may be accessed. Where separate indexing/advancement is envisaged separate actuation means (e.g. levers or buttons) may be provided to the dispenser to enable separate actuation thereof.

The dispensing mechanism herein comprises a receiving station for receiving each of the plural medicament carriers. Embodiments are envisaged both in which there is a single receiving station which is capable of receiving plural medicament carriers and also those in which each medicament carrier is received by a distinct (i.e. individual) receiving station. In the latter case, the individual receiving stations may either be coupled or not.

The dispensing mechanism further comprises a release for releasing a distinct medicament dose portion from each of the plural medicament carriers on its receipt by the receiving station. The release can have any suitable form. Where the elongate carrier is in the form of a blister pack, the release may for example, comprise means to rupture, puncture, tear or otherwise access the blister. In a particular preferred aspect, where the medicament carrier is in the form of a peelable blister strip the release comprises means for peeling apart the blister strip. In one aspect herein, each blister strip is peeled apart about a defined beak or wedge form feature of the dispenser.

An outlet is positioned to be in communication with the distinct medicament dose portions releasable by said a release to enable their dispensing to the patient. The outlet may have any suitable form. In one aspect, it has the form of a mouthpiece. In another aspect, it has the form of a nozzle for insertion into the nasal cavity of a patient.

The outlet is preferably a single outlet, which communicates with all of the distinct medicament dose portions on their release by said release. Communication is for example, via a common air channelling means (e.g. formed as an airpipe or common manifold). The patient may therefore breathe in through a single outlet, and that breath be transferred through the common air channelling means to (all of) the released medicament dose portions, thereby enabling their inhalation as a combined product. The outlet and/or channelling device may be shaped to encourage mixing of drug as a result of the airflow created by inhalation by the patient. For example, baffles or other mechanical aids to mixing may be incorporated. Venturi channelling of the airflow is also envisaged in embodiments. Helical form channels are envisaged.

The outlet is generally shaped to assist efficient docking with either the mouth or the nasal cavity of the patient. In aspects, shaping may be provided to promote good lip seal (e.g. transverse mouthpiece form) and user tongue interaction with the mouthpiece.

The mechanism also comprises an indexer for indexing (e.g. individually) the distinct medicament dose portions of each of the plural medicament carriers. Said indexing typically happens in sequential fashion, for example accessing dose portions sequentially arranged in series along the length of the elongate carrier. The indexing of each carrier may be arranged to occur in coupled fashion, that is to say each is indexed concurrently.

In a preferred aspect, the medicament carrier comprises a peelable blister strip. In this aspect, the release suitably comprises a peeler for peeling apart a base sheet and lid sheet of each peelable strip to open a pocket. Suitably, the peeler includes lid driver for pulling apart a lid sheet from a base sheet of a pocket that has been received at the opening station.

Preferably, there is provided a medicament dispenser for use with plural blister strip form medicament carriers, each having multiple distinct pockets for containing medicament dose portions, wherein said pockets are spaced along the length of and defined between two peelable sheets secured to each other, said dispenser having a dispensing mechanism for dispensing the medicament dose portions contained within said plural medicament carriers, said mechanism comprising, a) an opening station for receiving a pocket of each of said medicament carriers;

b) a peeler positioned to engage a base sheet and a lid sheet of a pocket which has been received in said opening station for peeling apart such a base sheet and lid sheet, to open such a pocket;

c) an outlet, positioned to be in communication with an opened pocket through which a user can access a medicament dose portion from such an opened pocket; and d) an indexer for individually indexing the distinct pockets of each of the plural medicament carriers.

In accord with the present invention, the medicament dispenser includes one or more of the improvement features described herein.

In one aspect, a common opening station is provided for receiving a pocket of each of said medicament carriers. In another aspect, distinct opening stations are provided for receiving a pocket of each medicament carrier. Suitably, the distinct opening stations are linked by a communicating passageway or other means for enabling the coming together of the separately released medicaments.

Generally, the opening station(s) are located at a fixed position within the dispenser. In one aspect however, the opening station(s) are movable within the dispenser. The positioning of the opening station(s) may therefore be varied during the course of operation of the dispenser e.g. to act as a compensating means to ensure uniform accessing of pockets over the entire length of a strip form medicament carrier.

In one aspect, each movable opening station comprises a chamber (e.g. of cruciform shape) that in use, moves to locate adjacent respective opened leading pockets of each blister strip. The chamber is suitably provided to a carrier (e.g. bobbin-shaped) that is movably mountable within the dispenser e.g. along a sprung axis.

In the dispenser, each peelable strip form medicament carrier is acted on by a peeler (i.e. peeling means). The peeler engages a base sheet and a lid sheet of a pocket that has been received at the opening station(s) for peeling apart the base sheet and lid sheet to open a pocket. In one aspect, each peelable strip form medicament carrier is acted on by common peeler. In other aspects, each peelable strip is acted on by its own (i.e. separate) peeler.

Suitably, the peeler includes a lid driver for providing pulling force to a lid sheet and a peel surface about which the lid sheet is pulled, these features in combination acting such as to pull apart a lid sheet and a base sheet of a pocket (e.g. on receipt at the opening station).

The lid driver may have many forms, as described herein. The peel surface about which the lid sheet is pulled typically comprises a defined beak or wedge form feature of the dispenser. It will be appreciated that the peel surface and lid driver will be located within the device to optimise the peeling force experienced by the peelable strip.

In one aspect, the lid driver comprises a wheel on which the lid sheet is wound up, said wheel having a effective winding surface which remains approximately constant when tension in the lid sheet increases. In one aspect, this is achievable by fashioning the lid driver in 'collapsible wheel' form wherein the wheel collapses (i.e. the diameter of the wheel itself decreases) as lid sheet becomes wound around it to give it an overall approximately constant effective winding diameter (as defined by the diameter of the wheel and the strip wound around it). Suitably, said 'collapsible wheel' comprises a plurality of resiliently flexible arms each extending there from at an angle with respect to a radius. The leading end of the lid sheet is looped over one of said resiliently flexible arms to secure the lid sheet to the wheel initially.

Alternatively, the lid driver comprises a wheel on which the lid sheet is wound up, said lid sheet wheel having an effective winding surface, the effective diameter of which increases after every use of the dispenser as the lid sheet winds around the wheel. Compensation means are then provided to compensate for this increase, which would otherwise lead to a variation in the tension experienced by the lid sheet over its length and hence a variation in its indexing over time.

In one aspect, there is provided a controller comprising means to limit the extent of movement of said lid driver, in order to control the length of medicament carrier peeled by said peeler. Hence, the medicament carrier is indexed by the same amount each time.

In another aspect, the dispenser comprises compensating means positioned between said opening station and said lid sheet wheel for reducing the length of said lid sheet therebetween to compensate for any increase in the diameter of the effective winding surface of the lid sheet wheel during use of the dispenser.

Suitably, the compensating means takes the form of a flexible member. The flexible member may take the form of a flexible elongate arm about which the lid sheet is fed. The arm may flex inwards as tension in the lid sheet increases, and thus shorten the length of lid sheet between the opening station and the lid driver.

Suitably, the flexible member is resilient so that on removal of tension from the lid sheet, the flexible member returns to its rest position. Thus, the internal mechanism can be reloaded with a new medicament carrier after the used carrier is removed.

In one aspect, the compensating means takes the form of a spring that reduces in length as tension increase in the lid sheet between the opening station and the lid driver. Typically a piston head is mounted on one end of the spring about which the lid sheet is fed. The other end of the spring may be fixed. As tension in the lid sheet increases the piston is driven down onto the spring. Preferably, the compensating means takes the form of a sprung-loaded tensioner.

In another aspect, the compensating means is positioned at the lid driver (e.g. lid sheet wheel). In particular, the compensating means act such as to vary (generally, to reduce) the drive function characteristics of the lid driver to compensate for any increase in the diameter of the effective winding surface of the wheel during use of the dispenser. Thereby, the medicament carrier is uniformly indexed (i.e. typically indexed by the same length of strip) as a result of each actuation of the dispensing mechanism, and the pocket opening action is also experienced uniformly.

Suitably, the compensating means comprises a torsion spring positioned at the lid driver (e.g. lid sheet wheel). Suitably, the lid driver takes a hub form and the torsion spring is accommodated such as to provide a torsion hub drive, which may itself be driven by gears. In one aspect, in use, the torsion spring is initially tense and the tension reduces as the lid driver receives lid sheet thereby also reducing its drive action on later-received lid sheet (i.e. that lid sheet towards the tail end of the medicament carrier).

Suitably, the lid driver is in the form of a 'vane hub' and the compensating means is provided by providing an inner wall of a drum form hub with multiple teeth and an insert locating within the drum, wherein the insert defines a central spindle and protruding vane arms, the ends of which normally interact with the teeth on the inner wall of the drum. The insert is rotatable relative to the drum, but that rotation only occurs when sufficient rotational force is applied to the drum to overcome the interaction of the teeth with the respective, resiliently flexible vane arms. The nature of this interaction therefore defines a slipping (i.e. clutch) force, which must be overcome for free rotation of the insert relative to the drum to occur. In the absence of the slipping force the drum and insert 1 are fixed relative to each other and rotatable as a single unit.

Suitably, the compensating means comprises a constant torque device positioned at the wheel. The constant torque device is arranged to slip at a pre-determined torque. In aspects, gearing is provided such that the effective winding surface diameter of the wheel is always greater than that required and the constant torque device slips to accommodate this whilst maintaining desired lid sheet tension.

It will have been appreciated that the compensating means functions such as to compensate for an increase in the diameter of the effective winding surface of the wheel during use of the dispenser. It will be appreciated that the initial effective winding surface and associated initial drive 'speed' of the wheel is principally a function of the (fixed) initial diameter of the wheel. Variations are envisaged herein where that initial effective winding surface is selected to define particularly selected initial drive characteristics of the wheel.

In one variation sometimes called 'one way take up' mode, the initial effective winding surface is selected such as to initially provide ideal (i.e. uniform) indexing of the medicament carrier. As lid sheet winds up around the wheel the effective winding surface increases and the compensating means acts such as to compensate for that increase.

In another variation sometimes called 'two way take up' mode, the initial effective winding surface is selected such as to initially provide non-ideal (i.e. non-uniform) indexing of the medicament carrier because the diameter of the lid sheet wheel is insufficiently great. As lid sheet winds up around the wheel the effective winding surface increases to an ideal diameter and then on further winding up continues to increase to a non-ideal (i.e. too great diameter). In this embodiment it will be appreciated that the degree and nature of compensation provided by the compensating means will vary over the winding up function. The compensating means initially acts such as to compensate for the insufficient wheel diameter. That compensation then decreases to zero at the point where the diameter of the effective winding surface is ideal. The compensation then progressively acts such as to compensate for a too great effective winding surface. This approach has the advantage of overall reducing the (average) compensating action (e.g. tension) experienced by the medicament carrier from a defined zero (i.e. the ideal) and enables the use of less powerful tensioning means (e.g. smaller springs). In a preferred aspect of this variation, the ideal effective winding surface diameter is selected to correspond approximately to the point at which half of the lid sheet is wound up on the wheel, in which case the average (i.e. mean) compensating action experienced is by the carrier over a full usage cycle is close to zero.

Alternatively, the compensating means comprises a clutch to adjust for any increase in the diameter of the effective winding surface of the lid driver during use of the dispenser. In one aspect, the clutch communicates with the an indexer and the lid driver, and comprises a gearing surface defining plural gear engagement positions; and plural gear teeth for engaging said plural gear engagement positions, wherein the plural gear teeth are arranged such that at any one time only a single gear tooth engages a single gear engagement position.

In use, the clutch acts to compensate for the increase in diameter of said effective winding surface of the lid driver. The clutch allows for slippage when the tension in the lid sheet is greater than the force required to peel apart the lid sheet and the base sheet.

It will be appreciated that in total, the clutch effectively defines a number of individual gear positions that is greater than the number of gear engagement positions. This is therefore advantageous over a traditional slipping clutch arrangement comprising intermeshing gear wheels, where the effective number of individual gear positions defined is either equal to, or no more than, the number of gear engagement positions defined by one of the gear wheels.

Suitably, the gearing surface and plural gear teeth are arranged such that the number of individual gear positions defined is equal to the number of gear engagement positions multiplied by the number of gear teeth. In one example, if the gearing surface defines 60 gear engagement positions and there are 6 gear teeth, then up to 360 individual gear positions are definable (e.g. 1° resolution on a rotating gear system).

Suitably, the gearing surface defines from 20 to 100, preferably from 40 to 80 gear engagement positions. Suitably, the number of gear teeth is from 2 to 20, preferably from 3 to 10.

In one aspect, the gear engagement positions are equally spaced (e.g. equidistantly spaced) and the gear teeth are offset (e.g. non-equidistantly spaced) relative thereto. Such offset arrangement maximises the number of effective individual gear positions that are capable of definition. An example of this aspect is a Vernier spring arrangement.

In another aspect, the gear engagement positions are also equally spaced (e.g. equidistantly spaced) and the gear teeth are located on a wobbling element capable of wobbling the gear teeth to plural offset (e.g. non-equidistantly spaced) positions. Such a wobbling offset arrangement also maximises the number of effective individual gear positions that are capable of being defined. An example of this aspect is the wobbling wheel arrangement.

In aspects, the clutch is non-integral with either of the lid driver or the indexer, but forms a separate interconnecting component.

Suitably, the gearing surface comprises a gear wheel. As used herein, the term gear wheel encompasses, for example, a wheel, spindle or spool. Suitably, the gear teeth may be arranged to be in ratchet form (i.e. enabling movement in one direction only). Suitably, the gearing surface and gear teeth are in biased (e.g. sprung) engagement.

In another aspect, the lid driver comprises a mangle. The lid sheet passes through two rotating wheels that act as a mangle and is gripped at the point of contact with the wheels. The used portion of the lid sheet is collected in a chamber after it has passed through the mangle.

In another aspect, the lid driver comprises a roller. Suitably said roller is composed of a polymeric rubber and is positioned next to a guide wall. Suitably said roller has a smooth surface. Alternatively said roller has a knurled surface. The roller grips the lid sheet as it passes from the point at which it is separated from the base sheet through the space between the roller and the guide wall and the used portion of the lid sheet is then collected in a chamber. The roller has the advantage over the mangle described above in that a greater degree of contact between the roller wheel and the lid sheet occurs—the lid sheet is squeezed through the roller and may pass around about ⅓ of the roller wheel. This provides a higher level of grip and pulling force than with a mangle. The force required to turn the roller is constant throughout the use of the device and does not vary according to how much of the lid sheet has been peeled away from the base sheet. This is in contrast to the wheel described above where the forces required to turn the wheel may vary due to the fact that the lid sheet is wound around the wheel. The lid sheet is not wound around the roller. The roller also has the advantage that the lid sheet does not have to be looped around or fixed to the roller before use of the device, therefore simplifying assembly of the device and reducing costs.

In another aspect, the lid driver comprises a lid spool. Suitably, the lid spool comprises a toothed wheel with a central upward cylindrical projection on which the lid sheet may be wound when it has been separated from the base sheet. The lid spool may have a mechanical gearing mechanism which is driven on actuation of the dispenser; the lid sheet is pulled away from the base sheet and wound onto the lid spool, causing the rotatable indexing wheel to turn and index the base sheet by one dose. An interlock coupling, as described supra, may be moved along the base of the rotatable indexing wheel until it fits into the next base recess. The positioning of the interlock coupling in this recess limits the movement of the lid spool to the distance between two pockets on the base sheet and therefore prevents the amount of lid sheet which is wound around the lid spool from increasing as the diameter of the lid spool is increased.

In another aspect, the lid driver comprises a spiked wheel. As the spiked wheel turns, the lid sheet is pulled over it and the spikes perforate parts of the lid sheet to improve the grip on the lid sheet. The lid sheet then passes out into a chamber where it collects.

In another aspect, the lid driver comprises a clamp system. The clamp system comprises at least one angled spring that is pivotable at one end and grips the lid sheet at the other end. The clamp system is moved in the direction that the lid sheet is to be pulled and grips the lid sheet, pulling it and therefore peeling it away from the base sheet. The clamp system is then moved back to its rest position. This results in the spring pivoting and clamping the lid sheet, therefore preventing the lid sheet from being further peeled from the base sheet.

In another aspect, the used portion of the lid sheet may be passed around rollers and fed back onto the used portion of the base sheet after the medicament has been accessed to join back onto the base sheet. The lid sheet may be coated with a sticky substance to aid resealing. The use of this mechanism saves space, as the used portions of the blister strip will be collected in the same area.

In another aspect, the unopened medicament carrier (e.g. coiled blister strip) may be surrounded by a constant force spring. Alternatively, the unused blister strip may be surrounded by an elastomeric band or band comprising a contractible material. The constant force spring, elastomeric band or band comprising a contractible material contracts as the coil reduces in size.

Suitably, the dispenser comprises a guide for guiding the lid sheet and base sheet along separate paths at the opening station. The lid sheet is passed around the guide portion onto the lid driver. In one aspect, the guide comprises a roller mechanism. The lid sheet is fed over the rollers onto the lid driver.

The mechanism includes an indexer for individually indexing the distinct pockets of each of the plural medicament carriers. Suitably, the an indexer comprises a rotatable index wheel having recesses therein, said index wheel being engageable with a medicament carrier in use with said medicament dispenser such that said recesses each receive a respective pocket of the base sheet of a blister strip in use with said medicament dispenser.

Suitably, the rotatable index wheel additionally comprises a series of indentations located at its base and spaced in between the recesses.

Suitably, the indexer additionally comprises an interlock coupling to couple actuation of the dispenser to the index wheel. The interlock coupling reversibly locks the index wheel in place. Preferably, said interlock coupling comprises a foot portion having a toe and a heel, and a tail section. Preferably, said interlock coupling is pivotally mountable to the dispenser at its foot portion. Preferably, said toe fits into one of the indentations on the rotatable index wheel. Preferably, the interlock coupling is sprung to bias it towards location of the toe in one of the indentations.

Alternatively, the indexer comprises a gear and sprocket wherein teeth on the wheel fit into apertures or holes formed on one or both edges of a medicament carrier. The mechanism therefore resembles that of photographic film being advanced through a camera.

Alternatively, the indexer comprises an index ratchet that is moveable between a locked position whereby said ratchet engages a pocket on said medicament carrier and prevents further peeling thereof, and a release position allowing free movement of said medicament carrier. In this embodiment, actuation of said medicament dispenser actuates said lid driver and releases said index ratchet from a medicament carrier to allow peeling thereof.

Suitably, the dispenser additionally comprises a first chamber in which at least one medicament carrier is initially housed and from which it is dispensed and a second chamber to receive the used portion of the base sheet after it has been indexed around the index wheel and separated from the lid sheet. Suitably, said first chamber and said second chamber are separable by a wall. In one aspect, said wall is movable to adjust the size of said first and second chambers. In another aspect, the wall is pivotally mountable. Alternatively the wall is slidably mountable.

Suitably, the internal mechanism further comprises a third chamber to receive the used portion of the lid sheet and a fourth chamber that houses the index ratchet. The fourth chamber may communicate via a slit, which in turn extends upwardly within a mouthpiece and communicates with air inlets.

Suitably, the dispenser additionally comprises a crushing wheel to crush the base sheet after the medicament has been removed from the pockets thereof. The crushing wheel therefore reduces the space that the used portion of the base sheet takes up.

The Applicant has now appreciated that it is advantageous if the dispensing mechanism is arranged such that it requires as little space as possible within the medicament dispenser, whilst not compromising its function.

In one aspect, space may be saved by reducing the size of the individual components of the dispensing mechanism or by arranging the components in a space efficient manner or by reducing the number of components, for example by employing a single component to perform multiple functions.

The Applicant has found that components that may be conveniently reduced in size include the lid driver (e.g. in torsion hub or collapsible wheel form) and the indexer (e.g. in index wheel form).

The Applicants have also found that rearrangement of the relative positioning of various components can be particularly beneficial.

In particular for space saving, it is has been found to be beneficial to position the lid driver (e.g. torsion hub) and peel surface (e.g. beak) of the peeler in close proximity (e.g. adjacent) to each other. Such an arrangement can also enhance the effectiveness of the peeling action of the peeler, particularly when combined with the other 'force modification' improvements described herein below.

For space saving, it has also been found to be beneficial to position the common opening station and air channelling means (e.g. in the form of a manifold) to the outlet quite deeply within the device (i.e. closer to a centrally located position than to an edge located position). Adopting this configuration enables the other component parts of the dispensing mechanism and carrier (e.g. see below) to be more efficiently located relative to each other.

The Applicants have also appreciated that a significant amount of space within the dispenser device is taken up by the plural medicament carriers (e.g. in elongate blister strip form). Overall space efficiency may therefore be improved by suitable configuration of the dispensing device to more effectively accommodate the medicament carriers. In particular, where the medicament carriers are in elongate blister strip form space efficiency may be improved by reconfiguration of the dispenser to in use, most effectively contain the unpeeled strips (i.e. lid and base sheets conjoined) and peelably separated and 'emptied of medicament' parts (i.e. 'waste' lid and base sheets).

In one space saving improvement it has been found to be advantageous to provide a means for tightly winding up either or both of the 'waste' lid sheet and base sheet of each medicament carrier. The 'waste' lid sheet typically winds up on the lid driver (e.g. torsion hub or collapsible wheel form). A rotatable waste spindle may additionally be provided to receive and tightly wind up each 'waste' base sheet. The waste spindle may be common for all medicament carriers or more typically, individual waste spindles are provided to receive 'waste' base sheet associated with each medicament carrier. Rotation of the medicament carrier is typically coupled to that of the indexer or peeler (or any driver therefor, including a movable cover provided to the dispenser device) to ensure an effective, suitably coupled winding up action.

In aspects, the movement of the 'waste' lid and/or base sheet take up means may be coupled to that of other component parts of the dispensing mechanism. In one aspect, the movement of the 'waste' lid and/or base sheet is arranged to be driven by the opening and/or closing of a rotatable cover provided to a housing of the medicament dispenser. In another aspect, the movement of the 'waste' lid and/or base sheet take up means is arranged to drive a mechanical counter wheel having dose count indicia provided on the periphery thereof.

In another space saving improvement the Applicant has appreciated that it is advantageous if each 'waste' base sheet is arranged for coiling up within a spiral track typically provided at the periphery of the dispenser device. Particular space savings are possible if for receipt of plural waste 'base sheets' the spiral tracks are arranged one inside the other (i.e. co-located in a spiral sense).

In a further space saving improvement the Applicant has appreciated that it is advantageous if both unpeeled strip and 'waste' base sheet are accommodated with a common (i.e. shared) chamber. Use of such a common chamber can however, potentially give rise to contamination problems if the inner cavity of the dispenser device housing that acts to house the dispensing mechanism, is not sealed off from the outside environment. Problems can particularly arise if there is the possibility of communication (e.g. air/powder flow) between the common chamber and the air channelling means, which channels powder from an opened pocket at the common opening station from the outlet for inhalation by a patient.

In one aspect, a medicament dispenser device is therefore provided herein, in which the common chamber (and parts of dispensing mechanism necessarily housed therein) are sealed off from the outside environment, and in which the air channelling means which leads to the outlet may only communicate with a defined number (usually, one) of opened pockets of each elongate form medicament carrier. Suitably, the air channelling means is in the form of a manifold, which includes an air inlet that in use, allows air to be drawn into the manifold and thence, into the opened pockets to aerosolise the powder for delivery to the inhaling patient. The form of the manifold may also be arranged to promote mixing of powder aerosolised from the opened pockets of each of the plural medicament carriers.

Thus, a suitable form of the manifold comprises a body defining an air channelling means, said body provided with an inlet for enabling ingress of air to said air channelling means; a docking port for docking with one or more opened pockets of one or more medicament powder carriers herein; and an outlet for enabling egress of aerosolised pockets from said one or more pockets. Mixing of powder may be encouraged by the shaping of the air channelling means and/or by the provision of features thereto (e.g. swirl promoting features) that encourage mixing.

In variations, the common chamber is partly or wholly sub-divided into a first chamber and second chamber by a curtain wall that is movable to adjust the relative size of said first and second chambers. The wall may in aspects, be pivotally mountable or slidably mountable. In an alternative, the curtain wall is replaced by a bag, which expands as it becomes filled (e.g. with 'waste' base sheet).

In another space saving aspect, the Applicant has found that it can be advantageous if one or more of the elongate form medicament carriers are in the form of a peelable strip and at least, the base sheet thereof is formed as a continuous loop. In variations, the lid sheet, which forms a peelable sealing lid to the base sheet, may either have continuous loop or non-continuous loop form.

Various forms of 'continuous loop' type embodiment are envisaged including those in which the continuous loops are arranged in opposing C-loop configuration; in opposing S-loop configuration; and in flattened loop type configurations. It will be appreciated that the form that the one or more loops defines within the dispenser device will be dictated by space efficiency within a defined housing shape in addition to dispensing functionality.

In one arrangement herein, first and second medicament-containing blister strips having base sheets in continuous loop form are positioned in 'caterpillar track arrangement' about respective multi-pocket index wheels and free-running rollers. The two index wheels are arranged to rotate in mutually opposing directions (i.e. one clockwise, the other anti-clockwise) such that within the dispenser the two loops travel in a mutually opposing rotary sense. In a particular aspect, the leading end of the lid foil of each strip joins to the base sheet of the other strip. The effect of this joining is that as each strip is rotated about its index wheel it results in the lid foil of the other strip being pulled away from its base sheet (e.g. over a peel surface to peelably separate the lid foil from the base sheet of that other strip and open the leading pocket thereof). In a further particular aspect, the mechanism may be arranged such that as the strip is further rotated about its index (e.g. as a result of subsequent pocket-opening operations) the detached (i.e. 'waste') lid foil thereof tends to associate (e.g. cling to) the base sheet of the other strip to which its end is joined. It will be appreciated that this arrangement negates the need for any particular 'waste' lid foil collecting area or component part to be provided to the dispenser, thereby saving space.

As previously described, the dispensing mechanism suitably comprises a peeler that includes a lid driver (e.g. a torsion hub) for providing pulling force to a lid sheet and a peel surface (e.g. a beak) about which the lid sheet is pulled. These features in combination act such as to peel apart a lid sheet and a base sheet of a pocket (e.g. on receipt at the opening station) of each elongate form medicament carrier.

The Applicant has appreciated that to reduce the force required to achieve the peeling action it is desirable that as much of the pulling force applied by the lid driver is translated into the peeling force necessary to peelably separate the lid sheet and base sheet. In particular, it is desirable that frictional losses are minimised.

Reduction of frictional losses may be achieved by making the path between and peel surface and lid driver as direct and non-tortuous (e.g. non-obstructed) as possible. In particular, it is desirable that the wrap angle (i.e. that angle defined between the direction of travel of the lid sheet when it leaves the peel surface and the direction of travel of the lid sheet at its point of take up by the lid driver) is minimised.

Reduction of frictional losses may also be achieved by selecting appropriate low friction materials (e.g. nylon or PTFE) for the peel surface and indeed the lid sheet, itself. Low friction coatings may be applied to achieve this effect.

Alternatively, reduction of frictional losses may be achieved by using a movable (e.g. rotatable) peel surface such as a beak in roller form, which rotates as lid sheet is pulled across it.

Any or all components of the dispensing mechanism may be driven by either an electronic or mechanical drive system or combination thereof.

Suitable mechanical drive systems typically include one or more actuators coupled via appropriate gearing (e.g. gear trains comprising multiple individual gears) to the drivable parts of the dispensing mechanism (e.g. the indexer, peeler and any 'waste' collection spindle). The one or more actuators may have simple lever form or have other forms that enable provision of mechanical advantage. In one aspect, the dispenser device is provided with a movable cover and movement of this cover acts to drivably actuate one or more components of the dispensing mechanism.

Suitably electronic drive means typically comprise a motor, preferably an electrically powered motor. The motor may provide linear or rotary drive, but in general, rotary motors are most suitable. The motor may for example, comprise a DC electric motor, a piezoelectric (PZ) motor, an ultrasonic motor, a solenoid motor or a linear motor. Preferably, the electronic drive system comprises a DC motor, a PZ motor or an ultrasonic motor.

The use of ultrasonic motors is particularly preferred since they offer advantages over conventional motors in terms of weight, size, noise, cost and torque generated. Ultrasonic motors are well known in the art and are commercially available (e.g. BMSTU Technological Cooperation Centre Ltd, Moscow, Russia; Shinsei Corporation, Tokyo, Japan).

Ultrasonic motors do not use coils or magnets but comprise a piezo-electric ceramic stator that drives a coupled rotor. The stator generates ultrasonic vibrations, which in turn causes rotation of the rotor. While regular DC motors are characterised by high speed and low torque, requiring reduction gearing to increase torque, ultrasonic motors attain low speed and high torque, thus eliminating the need for reduction gearing. Furthermore, these motors are lightweight and compact, lacking coils and magnets, and are noiseless as the ultrasonic frequencies used are not audible to the human ear.

Suitably, the dispenser further comprises actuating means for actuating a manual or electronic drive system. Said actuating means may take the form of a switch, push-button, or lever.

The medicament dispenser herein is typically provided with a housing to house the dispensing mechanism thereof and in which, the outlet is provided to the housing (e.g. as a mouthpiece for oral use or a nozzle for nasal use).

In one aspect, the housing is provided with a movable cover to reversibly cover the outlet. The cover is therefore movable from a first position in which it covers the outlet ('stowed position') to a second position in which the outlet is uncovered ('use position'). Embodiments are envisaged in which the movement of the cover is coupled (e.g. through suitable gearing) to move one or more parts of the dispensing mechanism such as the indexer, base sheet waste spool or dose counter.

In another aspect, housing is shaped such that it may be stood upright on a flat surface, thereby, for example enabling its ready storage on the bedside table of a patient. In one aspect, a base is provided to the housing for reading standing up thereon.

In one particular aspect, the dispenser herein is configured to be reloadable. In particular, each medicament carrier is suitably provided within a reloadable cassette.

In particular, the dispenser herein is configured to comprise a body; a holder, shaped to fit within said body and movable relative to said body; and receivable by said holder, a cassette containing plural elongate form medicament carriers.

Suitably, any drive system (e.g. electronic) is located in either the body or the holder part, and the cassette comprises the minimum number of component (i.e. internal mechanism) parts. In embodiments, the body/holder including the (e.g. electronic) drive is retainable by the user and the cassette is sold as a refill/reload component that is discarded after use. By locating an electronic drive system in the body/holder, the amount of electronic components that are discarded is minimised which is advantageous from an environmental standpoint.

Suitably, the cassette of the reloadable form medicament dispenser herein comprises a) an opening station for receiving a pocket of each of the plural form medicament carriers;

b) a peeler positioned to engage a base sheet and a lid sheet of a pocket which has been received In said opening station for peeling apart such a base sheet and lid sheet, to open such a pocket;

c) an outlet, positioned to be in communication with an opened pocket through which a user can access a medicament dose portion from such an opened pocket; and d) an indexer for individually indexing the distinct pockets of each of the plural medicament carriers.

Suitably, movement of the holder relative to the body results in movement of the cassette between a first position and a second position such that the cassette is reversibly removable from the holder when the cassette is in the second position.

Suitably the first position comprises a dispensing position. Preferably the second position comprises a non-dispensing position. The cassette is therefore only removable from the holder when the cassette is in the non-dispensing position.

Suitably, the holder and body include attaching means to attach the holder to the body. Preferably, said attaching means comprise a snap fit mechanism. Suitably said snap fit mechanism comprises a pin and hole system.

Suitably, the holder is pivotally movable relative to the body. Alternatively the holder is rotationally movable relative to the body.

Suitably the holder additionally comprises a stop to limit movement of the holder relative to the body. The stop abuts against the edge of the body at two points when it is rotated. At these points the holder may be designed to click into place. Therefore when the stop abuts one body edge then it is clicked into the dispensing position and when the stop abuts the other body edge then it is clicked into the non-dispensing position. Alternatively the holder is slidably movable relative to the body.

Suitably, the holder additionally comprises a catch to retain the cassette. The catch may for example comprise a sprung pin that fits into a hole or an integral catch that deforms when pressed allowing removal of the cassette.

Suitably, the catch is child resistant. Child resistance may be realized by having a system that forces the user to perform two actions at once to remove the cassette. Other features of the catch may include shock or impact resistance, the ability to lock the catch and orientation features to ensure that the cassette can only be inserted one way. The catch should also be easy to manufacture and assemble, be robust, be composed of a minimal number of components and intrude minimally into the space into which the cassette is inserted.

Suitably, the holder includes guide means to guide the cassette into the holder. Preferably said guide means comprise guide rails. Alternatively the guide means comprise grooves, indentations or other shaping or surface details to define a 'lock and key' relationship between the holder and the cassette. Colour guides, arrows and any other surface markings may also be employed.

Suitably, the cassette additionally comprises means to actuate the dispenser. The actuating means may take the form of a switch, push-button or lever.

Suitably, the cassette additionally comprises a mouthpiece. Suitably, said mouthpiece is extendable. The mouthpiece extends as the cassette and holder are moved from the non-dispensing position to the dispensing position. Alternatively the mouthpiece is retractable. The mouthpiece retracts as the cassette and holder are moved from the dispensing position to the non-dispensing position. In one aspect, the mouthpiece is telescopic. In another aspect, the mouthpiece is fixed.

The medicament dispenser may also be designed for nasal inhalation of a powdered medicament and may therefore incorporate a nozzle as an alternative to a mouthpiece. If the medicament is in solid form, the dispenser may incorporate an exit channel for tablet release.

Suitably, the body covers the mouthpiece and an indexer (and any actuator therefor) when the cassette is in the non-dispensing position. This avoids the need for a separate cover and protects the mouthpiece from the ingress of dirt and contaminants during storage.

Suitably, the cassette additionally comprises a raised portion to fit against the holder. The raised portion is located at the opposite end of the cassette to the mouthpiece/nosepiece/exit and indexing lever and prevents the incorrect insertion of the cassette into the holder since it is too wide to fit into the holder. The raised portion is shaped such that it fits against a cut away part of the holder. Preferably said raised portion includes a section that is raised to define a grip portion.

Suitably, at least a portion of the holder and body is shaped for ease of grip by the user.

The medicament dispenser in reloadable form may be supplied as a kit of parts. A first part of the kit comprises a body; a holder, shaped to fit within said body and movable relative to said body; and within said holder a receiving station for receipt of a cassette. A second part of the kit comprises a cassette containing plural elongate form medicament carriers and a dispensing mechanism for indexing said plural elongate forms medicament carriers, wherein the cassette is receivable by the receiving station and movement of the holder relative to the body results in movement of the cassette between a first position and a second position such that the cassette is reversibly removable from the receiving station when the cassette is in the second position. Suitably, the holder also comprises an electronic drive system for driving the indexing mechanism of the cassette.

In one aspect, the reloadable dispenser is assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the plural elongate form medicament carriers (e.g. blister strips) are inserted into the cassette. These may be wound into the dispenser before the lid is attached to the cassette and the cassette sealed. Alternatively, the cassette may be formed completely apart from a hole left in its side for insertion of the medicament carriers. The hole may then be sealed to complete the cassette. This second method of inserting the medicament carriers into the device has the advantage that it is much simpler.

Suitably, the medicament dispenser herein comprises an actuation or dose counter for counting the number of actuations of the indexing lever or releases of dose from the cassette. The dose counter may count the number of doses left to be taken or the number of doses taken. in one aspect, the dose counter is electronic. Alternatively said dose counter is mechanical.

In one aspect, the blister strip has printed numbers on it corresponding to the doses in the pockets. Preferably, said printed numbers are visible through a window in the body of the dispenser or any cassette reload therefor.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

The electronic data management system may be integral with the body of the dispenser. Alternatively, the electronic data management system forms part of a base unit that is reversibly associable with the body.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Energy may be conserved by a variety of means to enable the dispenser to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods is available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hardwired link, an infrared link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release. The time delay is typically of the order of from three to thirty seconds.

Suitably, the medicament dispenser additionally comprises a release detector for detecting release of medicament from the cassette, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analyzed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion from the first transceiver to the second transceiver. The data is preferably in digital form and suitable for transfer by electronic or optical means.

One advantage of embodiments of this type is the ability to store many types of information in different parts of the memory structure of the transceivers. The information is furthermore stored in a form that is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory that uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the medicament dispenser with a cassette the second transceiver may, for example, read the unique serial number, batch code and expiry date of the medicament and any other information on the second transceiver. In this way the nature and concentration of the medicament, together with the number of doses used or remaining within the cassette, may be determined. This information can be displayed to the patient on a visual display unit. Other information, such as the number of times the medicament dispenser has been reloaded with a cassette, may also be displayed.

Similarly, should the cassette be removed from the holder before the supply of medicament is exhausted, the same data can be read from the second transceiver and the number of doses remaining or used determined. Other information, such as the date and time of administration of the drug, or environmental exposure data such as the minimum/maximum temperatures or levels of humidity the cassette has been exposed to, may also be read and displayed to the user.

In the event that the supply of medicament within the container becomes exhausted, or that the shelf life of the medicament has expired, or that the first transceiver does not recognize the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the dispenser. Or alternatively, data may be stored in a database memory of the electronic data management system and periodically downloaded to any transceiver. In either case, a history of the usage of the dispenser may be built up in the memory of a transceiver.

In one embodiment herein, a history of the usage of the medicament dispenser is transferred to the second transceiver. When the medicament carriers in the cassette are exhausted, the cassette is exchangeable by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure that allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medicament dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly powered and the term passive is used to mean indirectly powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labeling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or holder of the medicament dispenser or on the cassette.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is moldable or wieldable to the cassette or housing. Suitably, the carrier encases the tag. More preferably, the carrier forms a hermetic seal for the tag. In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas instruments of the United States of America under the trade mark Tagit. Suitably, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet that may in embodiments be capable of receiving printed text thereon.

In one aspect, the first transceiver is integral with the body such that a single unit is comprised. The first transceiver may for example be encased within or molded to the body.

In another aspect, the first transceiver forms part of a base unit that is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications No.s PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard that employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be a traditional copper wire system, a cellular system or an optical network.

In another aspect, the network computer system comprises a private access network computer system. The private access network system may for example, comprise an Intranet or Extranet that may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto.

More preferably, information from the user-specific network address can be made available to the remote information source.

In one aspect, the remote information source is a medicament prescriber, for example a doctor's practice. Information transferred from the medicament prescriber may thus, comprise changes to prescription details, automatic prescription updates or training information. Information transferred to the medicament prescriber may comprise compliance information, that is to say information relating to the patient's compliance with a set-prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests that have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

Suitably, the medicament dispenser additionally comprises a geographic positioning system such as a global positioning system or a system that relies on the use of multiple communications signals and a triangulation algorithm.

According to another aspect of the present invention, there is provided a medicament dispenser for containing plural elongate form medicament carriers, each having multiple distinct medicament dose portions carried thereby, said dispenser having a housing, and within said housing a dispensing mechanism for dispensing the distinct medicament dose portions carried by each of said plural medicament carriers, said mechanism comprising, a) at least one receiving station for receiving each of the plural medicament carriers;

b) a release for releasing in combination a distinct medicament dose portion from each of the plural medicament carriers on receipt thereof by said receiving station;

c) an outlet, positioned to be in communication with the distinct medicament dose portions releasable by said release; and d) at least one indexer for individually indexing the distinct medicament dose portions of each of the plural medicament carriers, wherein said dispenser further comprises a movable cover that couples to the dispensing mechanism such that movement of said cover actuates one or more components of the dispensing mechanism.

According to a further aspect of the present invention there is provided the use of the dispenser herein for dispensing a combination medicament product.

BRIEF DESCRIPTION OF THE DRAWINGS

The invention will now be described with reference to the accompanying drawings in which:

FIG. 6a shows a sectional plan view of a further medicament dispenser in accord with the invention capable of receiving medicament carriers with base sheets in continuous loop form and FIG. 6b shows a section plan view of a simplified form of the medicament dispenser of FIG. 6a with medicament carriers received thereby;

FIGS. 9 and 10 show schematic plan views of further medicament dispensers in accord with the invention;

FIG. 12a shows a side view of a medicament carrier arrangement suitable for use in fold-up configuration, as shown in FIG. 12b; and FIG. 12c shows a medicament dispenser for receiving the carrier in fold-up configuration of FIG. 12b;

DETAILED DESCRIPTION OF THE DRAWINGS

Figure 1:
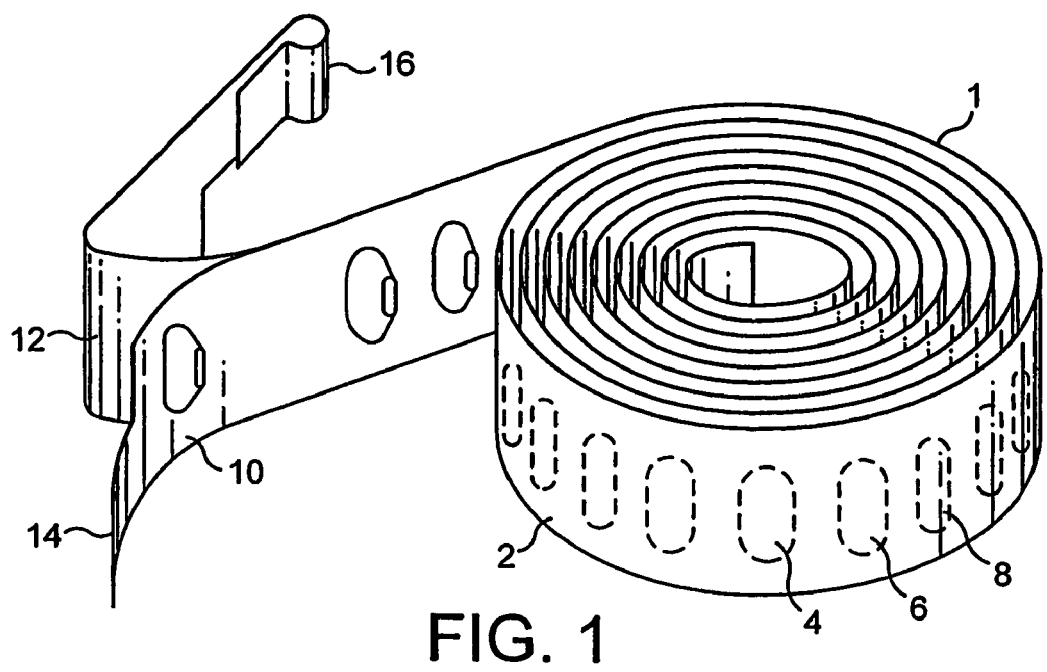
FIG. 1 shows a perspective view of a medicament carrier suitable for use in accord with the dispenser of the present invention.

FIG. 1 shows a medicament carrier 1 suitable for use in accord with the present invention. The medicament carrier comprises a flexible strip 2 defining a plurality of pockets 4, 6, 8 each of which contains a portion of a dose of medicament of a form suitable for inhalation and in the form of powder. In accord with the present invention, plural such strips 2 are typically employed in a single medicament dispenser, wherein each strip provides the component medicament dose portions of a combination medicament product. Each strip may be of the same size and/or contain the same dose amount (e.g. volume or mass) or in alternative embodiments, strips of different sizes and/or containing different dose amounts may be employed in combination.

The strip comprises a base sheet 10 in which blisters are formed to define the pockets 4, 6, 8 and a lid sheet 12 which is hermetically sealed to the base sheet except in the region of the blisters in such a manner that the lid sheet 12 and the base sheet 10 can be peeled apart. The sheets 10, 12 are sealed to one another over their whole width except for the leading end portions 14, 16 where they are preferably not sealed to one another at all.

The lid 12 and base 10 sheets are each formed of a plastics/aluminium laminate and are suitably adhered to one another by heat sealing. The lid sheet 12 comprises at least the following successive layers: (a) paper; adhesively bonded to (b) polyester; adhesively bonded to (c) aluminium foil; that is coated with a heat seal lacquer for bonding to the base sheet. The base sheet 10 comprises at least the following successive layers: (a) oriented polyamide (OPA); adhesively bonded to (b) aluminium foil; adhesively bonded to (c) a third layer comprising a polymeric material (e.g. polyvinyl chloride).

The strip 2 is shown as having elongate pockets 4, 6, 8 that run transversely with respect to the length of the strip 2. This is convenient in that it enables a large number of pockets 4, 6, 8 to be provided in series arrangement along a given strip 2 length. The strip 2 may, for example, be provided with thirty, sixty or one hundred pockets but it will be understood that the strip 2 may have any suitable number of pockets.

Figure 2:
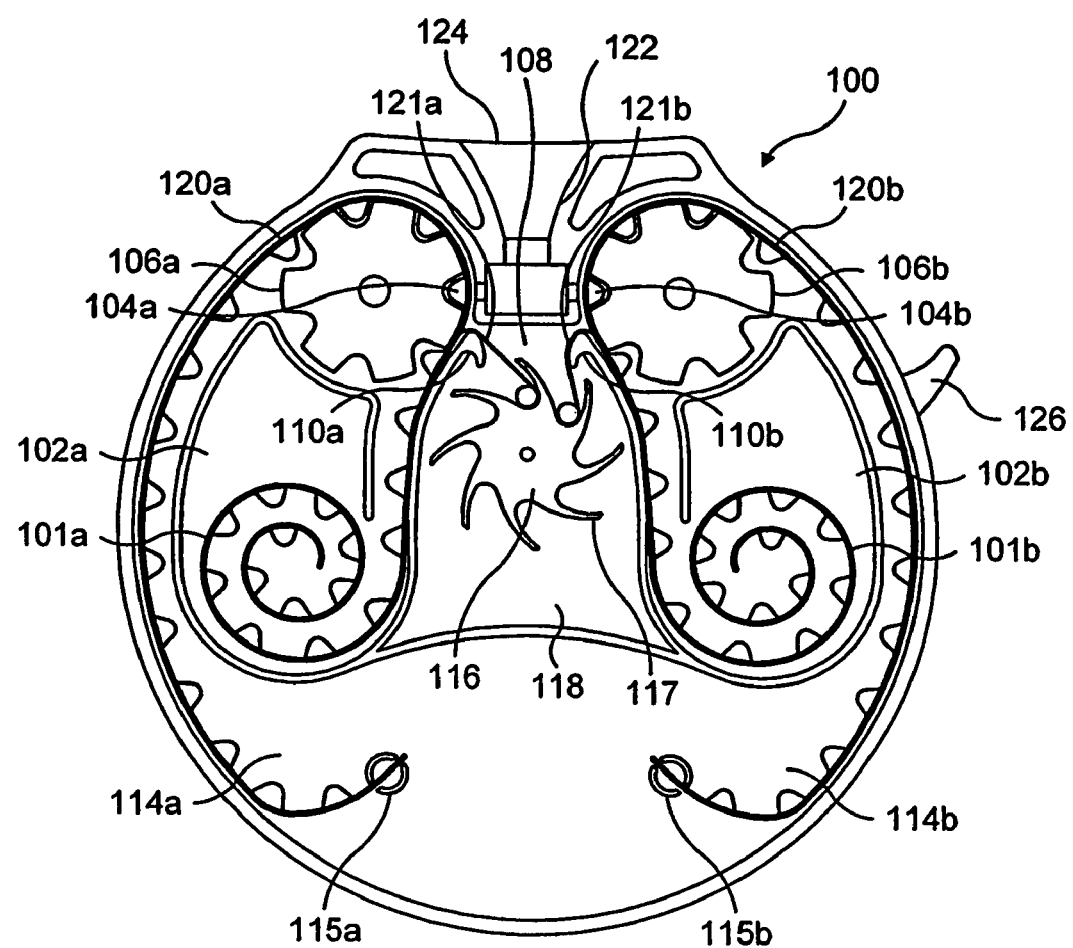
FIGS. 2 and 3 show sectional plan views of medicament dispensers in accord with the invention.

FIG. 2 illustrates a sectional view of the inner workings of a base unit of medicament dispenser 100 according to one aspect of the invention. In use, a protective cover (not shown) would be provided to the base unit 100. First and second medicament-containing blister strips 101a, 101b are positioned within respective left and right chambers 102a, 102b of the base unit 100. Each blister strip 101a, 101b engages in respective multi-pocket index wheel 106a, 106b, and successive pockets are thereby guided towards a central opening station 108. Rotation of the index wheels 106a, 106b is coupled together. At the opening station 108, the lid foil 120a, 120b and base foil 121a, 121b parts of each strip 101a, 101b are peelably separable about beak 110a, 110b. The resulting empty base foil 121a, 121b coils up in respective base take-up chambers 114a, 114b. Rotatable base foil anchor spindle 115a, 115b anchors the end of each respective base foil 121a, 121b in its chamber 114a, 114b. Progressive rotation of each respective anchor spindle 115a, 115b results in the 'waste' base foil 121a, 121b being wound up there around into a tight coil. Typically, the rotation of each base spindle 115a, 115b is coupled to that of the respective index wheel 106a, 106b. The used lid foil 120a, 120b feeds over its respective beak 110a, 110b and coils about common lid take-up spindle 116 (which is also arranged for rotation) in the common lid take-up chamber 118.

It will be noted that common lid take-up spindle 116 comprises plural arms 117 that splay out radially from the centre to give it an overall 'collapsible wheel' form. In use, as lid-foil 120a, 120b wraps around the rotating spindle 116, the arms 117 collapse inwardly thereby reducing the diameter of the spindle 116 itself but acting to maintain a roughly constant effective winding diameter as defined by the diameter of the spindle 116 in combination with the used lid foil 120a, 120b wrapped there around. The maintenance of this constant effective winding diameter ensures uniform indexing of each strip 101a, 101b over the entire strip length.

In use, the dispenser is primed by actuating lever 126 located on the side of the dispenser to drivably rotate the index wheels 106a, 106b and lid-take up spindle 116 to advance each blister strip 101a, 101b, thereby causing the leading pocket 104a, 104b thereof to be peeled open. To access the contents of the opened pockets 104a, 104b, the patient then breathes in through the outlet 124. This results in negative pressure being transmitted through manifold 122 to the opened leading pocket 104a, 104b of each strip 101a, 101b at the opening station 108. This in turn, results in the medicament powder contained within each of the opened pockets 104a, 104b being drawn out through the common manifold 122 to the outlet 124 and hence to the patient as an inhaled combination medicament dose. It be appreciated that, mixing of each separately delivered component of the combined medicament product happens as the powder is transported from each opened pocket 104a, 104b to the outlet 124.

Importantly, the dispenser of FIG. 2 enables different medicament types to be stored separately in each of the strips 101a, 101b but allows for the release and delivery thereof to the patient via the single outlet 124 as a combined inhaled product.

Figure 3:
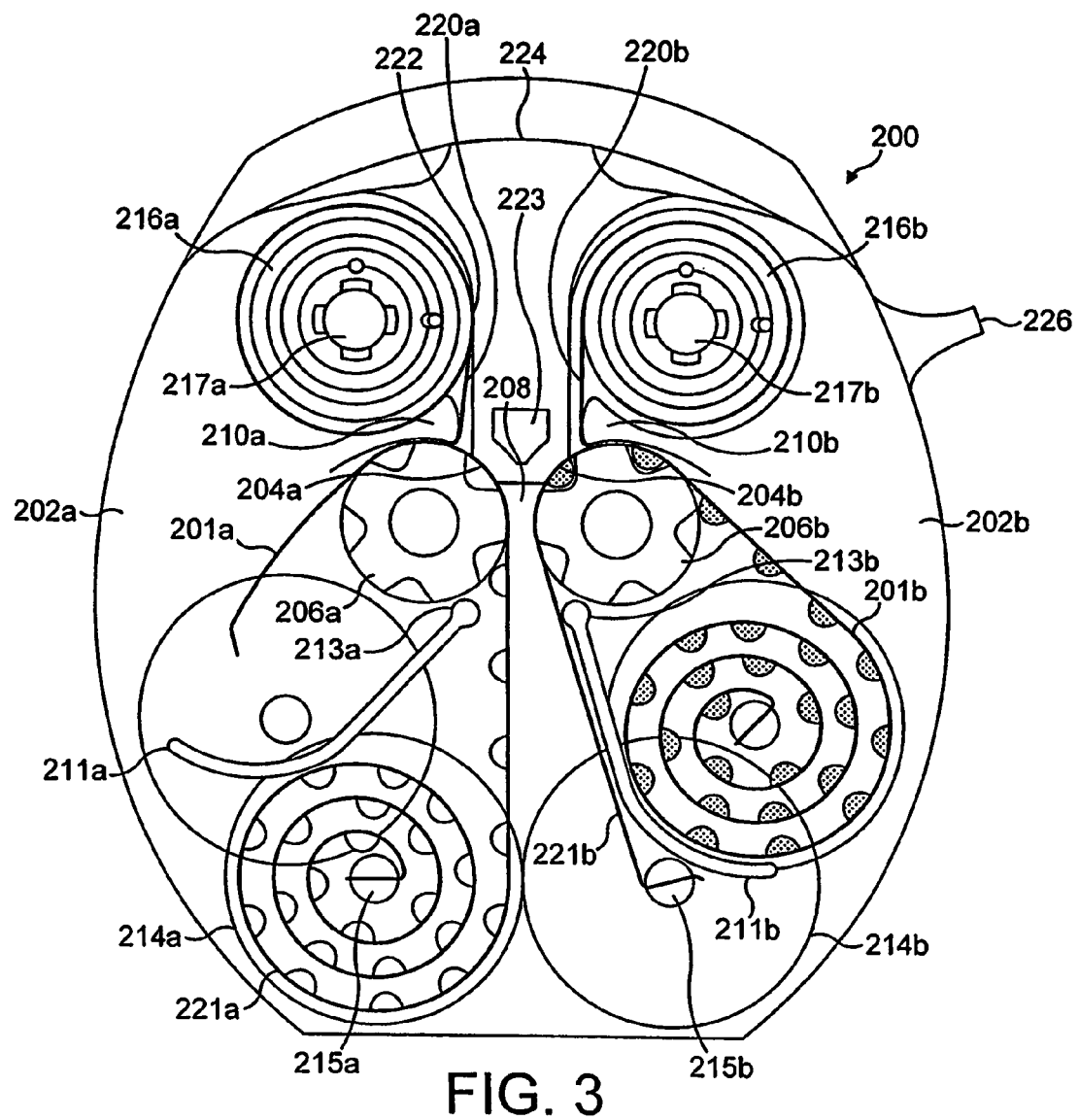

FIG. 3 illustrates a sectional view of the dispensing mechanism of a base unit of medicament dispenser 200 according to another aspect of the invention. In use, a protective cover (not shown) would be provided to the base unit 200 to provide a sealed cavity housing for parts of the dispensing mechanism of the dispenser 200 and blister strips 201a, 201b contained there within.

First and second medicament-containing blister strips 201a, 201b are positioned within respective left and right chambers 202a, 202b of the base unit 200. As shown, the first medicament strip 201a is shown in the 'fully empty' of medicament (i.e. end of life) configuration and the second medicament strip 201b is shown in the 'fully charged' with medicament (i.e. start of life) configuration. It will be appreciated, that this is necessarily an artificial view since in use, both strips will typically be equally full or empty (i.e. their configurations mirror one other). This artificial view is thus, used for illustration only in order that the configuration of the dispensing mechanism of the device 200 may be understood as the strip 201a, 201b travels through the device.

Each blister strip 201a, 201b engages in its respective five pocket index wheel 206a, 206b, and successive pockets are thereby guided towards a central opening station 208. The rotation of the index wheels 206a, 206b is suitably coupled together. At the opening station 208, the lid foil 220a, 220b and base foil 221a, 221b parts of each strip 201a, 201b are peelably separable about beak 210a, 210b. The resulting empty base foil 221a, 221b coils up in respective base take-up chambers 214a, 214b. Rotatable base foil anchor spindle 215a, 215b anchors the end of each respective base foil 221a, 221b in its chamber 214a, 214b. Progressive rotation of each respective anchor spindle 215a, 215b results in 'waste' base foil 221a, 221b being wound up there around into a tight coil. Typically, the rotation of each base spindle 215a, 215b is coupled to that of the respective index wheel 206a, 206b.

Flexible arms 211a, 211b pivoted at pivot points 213a, 213b are provided to each respective base take-up chamber 214a, 214b and act as a movable wall thereto. It will be seen that in the 'fully charged' (i.e. start of life) position of the right hand side of the dispenser 200 the flexible arm 211b acts on the medicament-charged strip 201b to compress it into a minimum space. In the 'fully empty' (i.e. end of life) position of the left hand side of the dispenser 200 the flexible arm 211a acts on the 'waste' base foil 221a to again compress it into a minimum space. The flexible arms 211a, 211b thereby act overall to reduce the space occupied by the strip 201a, 201b (when full or empty) in the dispenser device 200.

The used lid foil 220a, 220b feeds over its respective beak 210a, 210b and coils about respective lid take-up spindles 216a, 216b, which also rotate to wind up lid foil 220a, 220b thereon. Each lid take-up spindle 216a, 216b is provided with a centrally located torsion spring 217a, 217b. The function of the torsion spring 217a, 217b is to ensure a roughly constant driving tension is provided to each strip 201a, 201b by its lid take-up spindle 216a, 216b over the course of each entire strip length. In particular, each torsion spring 217a, 217b acts to compensate for the variation in drive tension associated with the increase in the effective winding diameter of each lid take-up spindle 216a, 216b as used lid foil 220a, 220b gradually becomes wrapped there around. Thus, uniform indexing of each strip 201a, 201b may be maintained over the entire strip length.

In use, the dispenser is primed by actuating lever 226 located on the side of the dispenser to drivably rotate (e.g. by use of a suitable gear arrangement) the index wheels 206a, 206b and lid-take up spindles 216a, 216b to advance each blister strip 201a, 201b, thereby causing the leading pocket 204a, 204b thereof to be peeled open and brought into communication with manifold 222, which itself communicates with mouthpiece-form outlet 224. As previously mentioned, the inner workings and blister strips 201a, 201b of the dispenser 200 are comprised within a sealed housing. Only the leading pockets 204a, 204b of each strip 201a, 201b may therefore communicate with the manifold 222 and thence to the outside environment via the outlet 224. Air inlet 223 is provided to the manifold 222 to assist in aerosolising medicament in the opened pockets 204a, 204b as described below.

To access the medicament contents of the opened pockets 204a, 204b, the patient breathes in through the outlet 224. This results in air being drawn into the manifold 222 through the air inlet 223 thereof, and that air being through manifold 222 to the opened leading pocket 204a, 204b of each strip 201a, 201b at the opening station 208. In turn, this results in the medicament powder contained within each of the opened pockets 204a, 204b being aerosolised and guided through the common manifold 222 to the outlet 224 and hence to the patient as an inhaled combination medicament dose. It be appreciated that, mixing of each separately delivered component of the combined medicament product happens as the powder is transported from each opened pocket 204a, 204b to the outlet 224. In embodiments, the manifold 222 is shaped to promote such mixing.

Figure 4A:
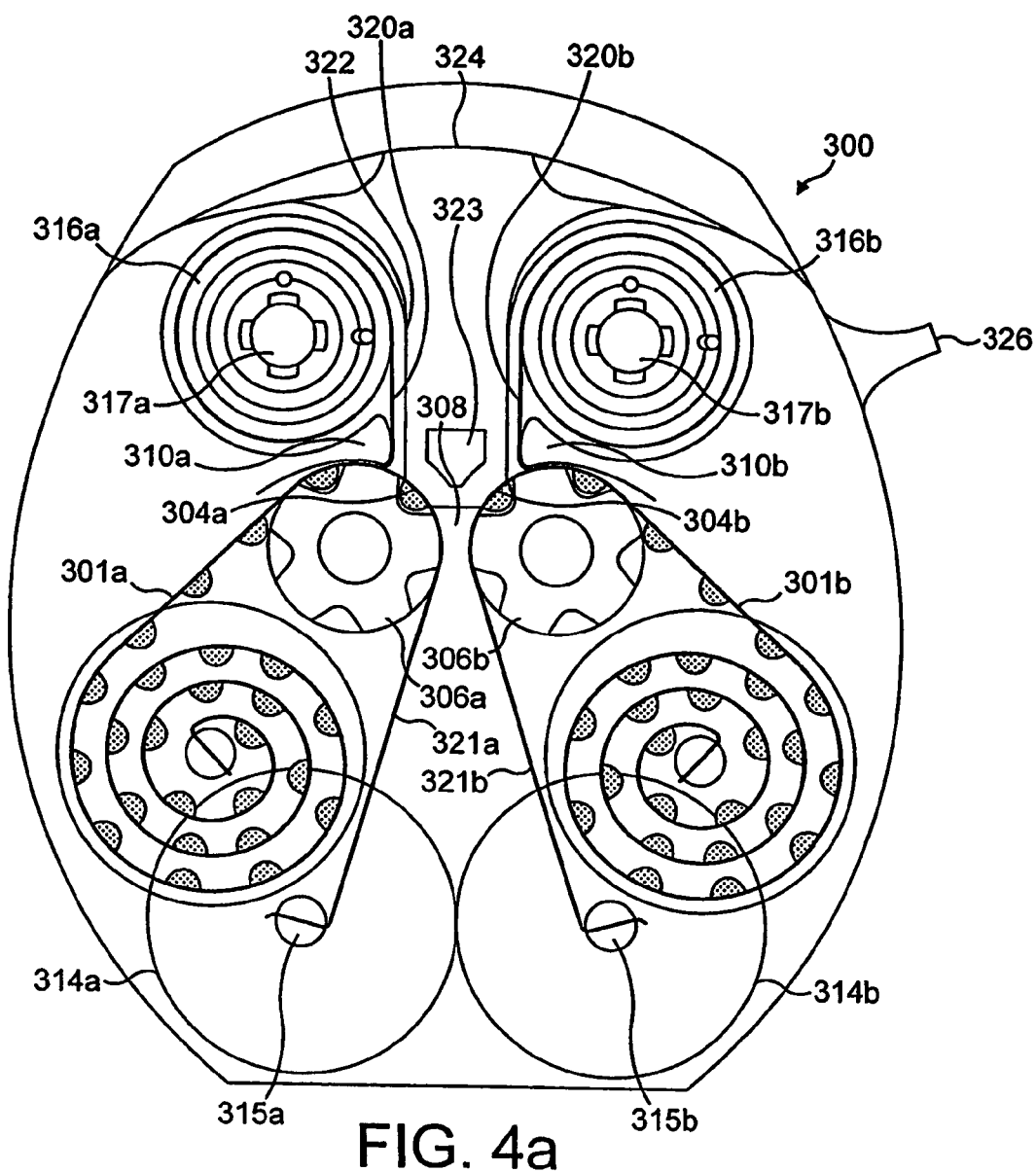
FIGS. 4a and 4b show sectional plan views of a medicament dispenser in accord with one aspect of the invention respectively in 'fully charged' with medicament and 'fully empty' of medicament configurations.
Figure 4B:
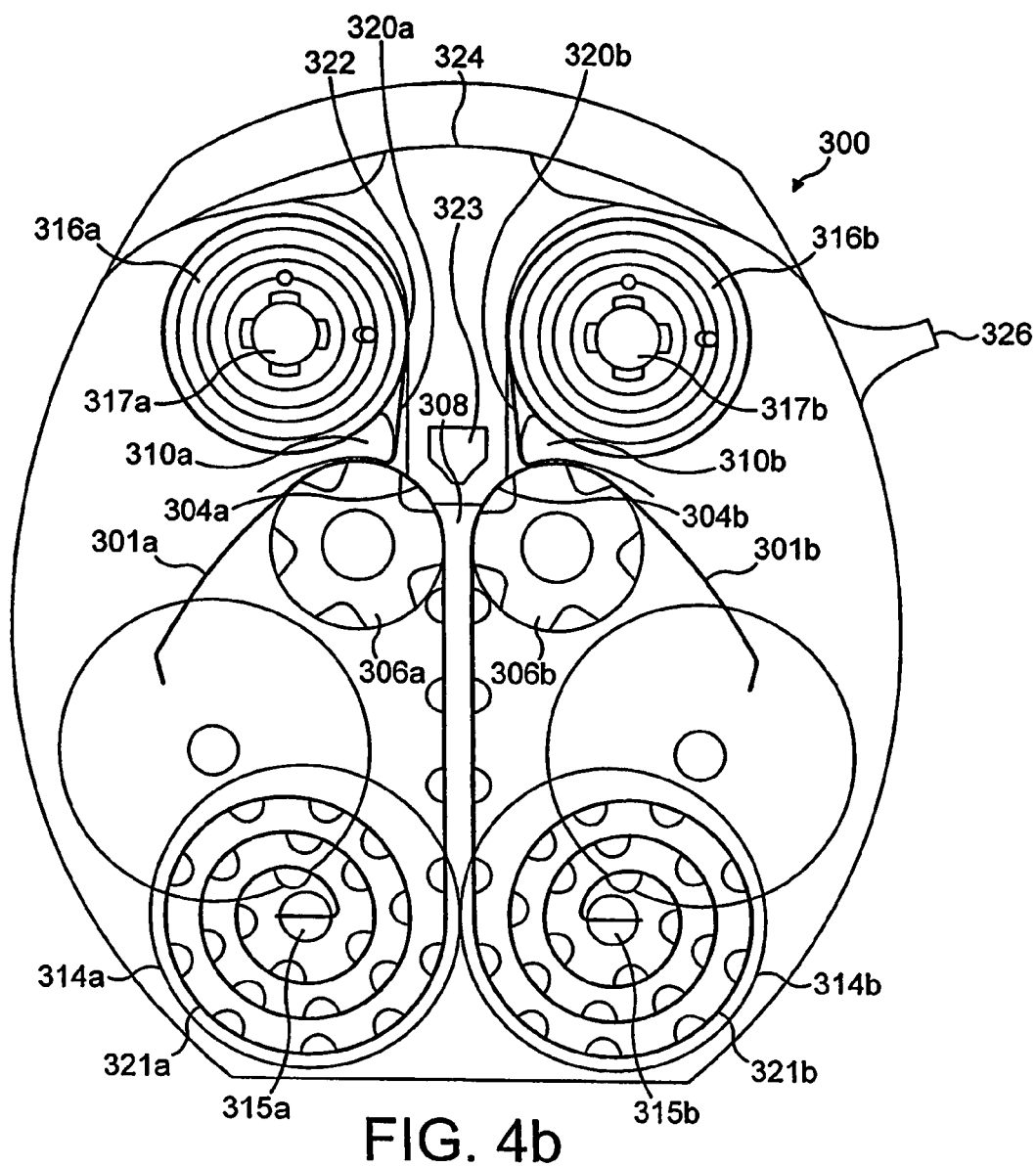

FIGS. 4a and 4b illustrate sectional views of the inner workings of medicament dispenser 300 according to another aspect of the invention. In use, a protective cover (not shown) would be provided to the base unit 300 to provide a sealed cavity housing for the parts of the dispensing mechanism and blister strips 301a, 301b contained there within.

First and second medicament-containing blister strips 301a, 301b are positioned within respective left and right chambers 302a, 302b of the base unit 300. In FIG. 4a, the medicament strips 301a, 301b are both in the 'fully charged' with medicament (i.e. start of life) configuration. In FIG. 4b, the medicament strips 301a, 301b are both in the 'fully empty' of medicament (i.e. end of life) configuration.

Each blister strip 301a, 301b engages in its respective five pocket index wheel 306a, 306b, and successive pockets are thereby guided towards a central opening station 308. The rotation of the index wheels 306a, 306b is suitably coupled together. At the opening station 308, the lid foil 320a, 320b and base foil 321a, 321b parts of each strip 301a, 301b are peelably separable about beak 310a, 310b. The resulting empty base foil 321a, 321b coils up in respective base take-up chambers 314a, 314b. Rotatable base foil anchor spindle 315a, 315b anchors the end of each respective base foil 321a, 321b in its chamber 314a, 314b. Progressive rotation of each respective anchor spindle 315a, 315b results in 'waste' base foil 321a, 321b being wound up there around into a tight coil. Typically, the rotation of each base spindle 315a, 315b is coupled to that of the respective index wheel 306a, 306b.

The used lid foil 320a, 320b feeds over its respective beak 310a, 310b and coils about respective lid take-up spindles 316a, 316b, which also rotate to wind up lid foil 320a, 320b thereon. Each lid take-up spindle 316a, 316b is provided with a centrally located torsion spring 317a, 317b. The function of the torsion spring 317a, 317b is to ensure a roughly constant driving tension is provided to each strip 301a, 301b by its lid take-up spindle 316a, 316b over the course of each entire strip length. In particular, each torsion spring 317a, 317b acts to compensate for the variation in drive tension associated with the increase in the effective winding diameter of each lid take-up spindle 316a, 316b as used lid foil 320a, 320b gradually becomes wrapped there around. Thus, uniform indexing of each strip 301a, 301b may be maintained over the entire strip length.

In use, the dispenser is primed by actuating lever 326 located on the side of the dispenser to drivably rotate the index wheels 306a, 306b and lid-take up spindles 316a, 316b to advance each blister strip 301a, 301b, thereby causing the leading pocket 304a, 304b thereof to be peeled open and brought into communication with manifold 322, which itself communicates with mouthpiece-form outlet 324. As previously mentioned, the inner workings and blister strips 301a, 301b of the dispenser 300 are comprised within a sealed housing. Only the leading pockets 304a, 304b of each strip 301a, 301b may therefore communicate with the manifold 322 and thence to the outside environment via the outlet 324. An air inlet 323 is provided to the manifold 322 to assist in aerosolising medicament in the opened pockets 304a, 304b as described below.

To access the medicament contents of the opened pockets 304a, 304b, the patient breathes in through the outlet 324. This results in air being drawn into the manifold 322 through the air inlet 323 thereof, and that air being through manifold 322 to the opened leading pocket 304a, 304b of each strip 301a, 301b at the opening station 308. In turn, this results in the medicament powder contained within each of the opened pockets 304a, 304b being aerosolised and guided through the common manifold 322 to the outlet 324 and hence to the patient as an inhaled combination medicament dose. It be appreciated that, mixing of each separately delivered component of the combined medicament product happens as the powder is transported from each opened pocket 304a, 304b to the outlet 324. In embodiments, the manifold 322 is shaped to promote such mixing.

By making reference to both FIGS. 4a and 4b the amount and position of the space occupied by each strip 301a, 301b may be appreciated as the strip 301a, 301b travels through the device. In general terms, in the 'fully charged' (i.e. start of life) configuration the bulk of space is occupied by coils of charged strip 301a, 301b. In the 'fully empty' (i.e. end of life) configuration the bulk of space is occupied by coils of empty base foil 321a, 321b. The locus of the 'occupied' space may also be seen to shift slightly (i.e. downwards and to the central axis, as illustrated) as the strip 301a, 301b travels through the device.

Figure 5:
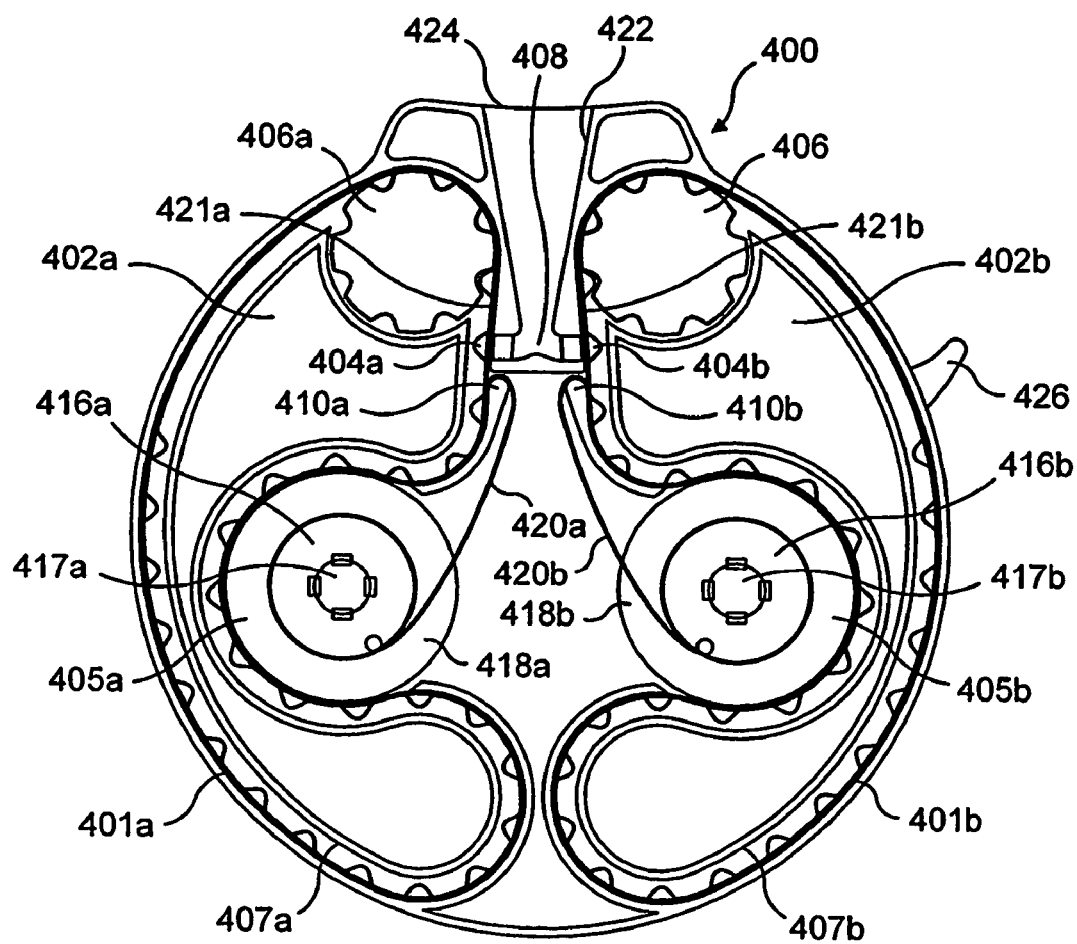
FIG. 5 shows a sectional plan view of a further medicament dispenser in accord with the invention having medicament carriers with base sheets in continuous loop form.

FIG. 5 illustrates a sectional view of base unit 400 of a medicament dispenser according to the invention. In use, a protective cover (not shown) would be provided to the base unit 400. First and second medicament-containing blister strips 401a, 401b are positioned about left and right lobes 402a, 402b of the base unit 400. Each blister strip 401a, 401b has a continuous loop form. That is to say, each strip comprises a continuous loop of base foil 421a, 421b having pockets 404a, 404b for containing medicament arranged along the majority of its length; and a strip of lid foil 420a, 420b provided to the base foil 421a, 421b to initially seal at least all of the pockets 404a, 404b. Within the dispenser the strip 401a, 401b snakes around hub 405a, 405b and guiding wall 407a, 407b that generally act to define the shape of each loop 401a, 401b when housed in the dispenser unit 400.

Each blister strip 401a, 401b engages in respective multi-pocket index wheel 406a, 406b, and successive pockets are thereby guided towards a central opening station 408. The rotation of the index wheels 406a, 406b is optionally coupled together. At the opening station 408, the lid foil 420a, 420b and base foil 421a, 421b parts of each strip 401a, 401b are peelably separable about beak 410a, 410b. In contrast to the embodiment of FIG. 2 (for example), the resulting empty base foil 421a, 421b is not coiled up. Rather, because it is joined (in 'continuous loop' fashion) to the tail end of the strip 401a, 401b it continues to be transported through the dispenser as the strip 401a, 401b is further advanced. The need for any distinct base foil take-up chamber (e.g. see chambers 114a, 114b of FIG. 2) is thereby avoided.

The used lid foil 420a, 420b feeds over its respective beak 410a, 410b and coils about respective lid take-up spindles 416a, 416b in respective common lid take-up chambers 418a, 418b, which also rotate to wind up lid foil 420a, 420b thereon. Each lid take-up spindle 416a, 416b is provided with a centrally located torsion spring 417a, 417b. The function of the torsion spring 417a, 417b is to ensure a roughly constant driving tension is provided to each strip 401a, 401b by its lid take-up spindle 416a, 416b over the course of each entire strip length. In particular, each torsion spring 417a, 417b acts to compensate for the variation in drive tension associated with the increase in the effective winding diameter of each lid take-up spindle 416a, 416b as used lid foil 420a, 420b gradually becomes wrapped there around. Thus, uniform indexing of each strip 401a, 401b may be maintained over the entire strip length.

In use, the dispenser is primed by actuating lever 426 located on the side of the dispenser to drivably actuate the index wheels 406a, 406b to advance each blister strip 401a, 401b, thereby causing the leading pocket 404a, 404b thereof to be peeled open. To access the contents of the opened pockets 404a, 404b, the patient then breathes in through the outlet 424. This results in negative pressure being transmitted through manifold 422 to the opened leading pocket 404a, 404b of each strip 401a, 401b at the opening station 408. This in turn, results in the medicament powder contained within each of the opened pockets 404a, 404b being drawn out through the common manifold 422 to the outlet 424 and hence to the patient as an inhaled combination medicament dose. It be appreciated that, mixing of each separately delivered component of the combined medicament product happens as the powder is transported from each opened pocket 404a, 404b to the outlet 424.

Figure 6B:
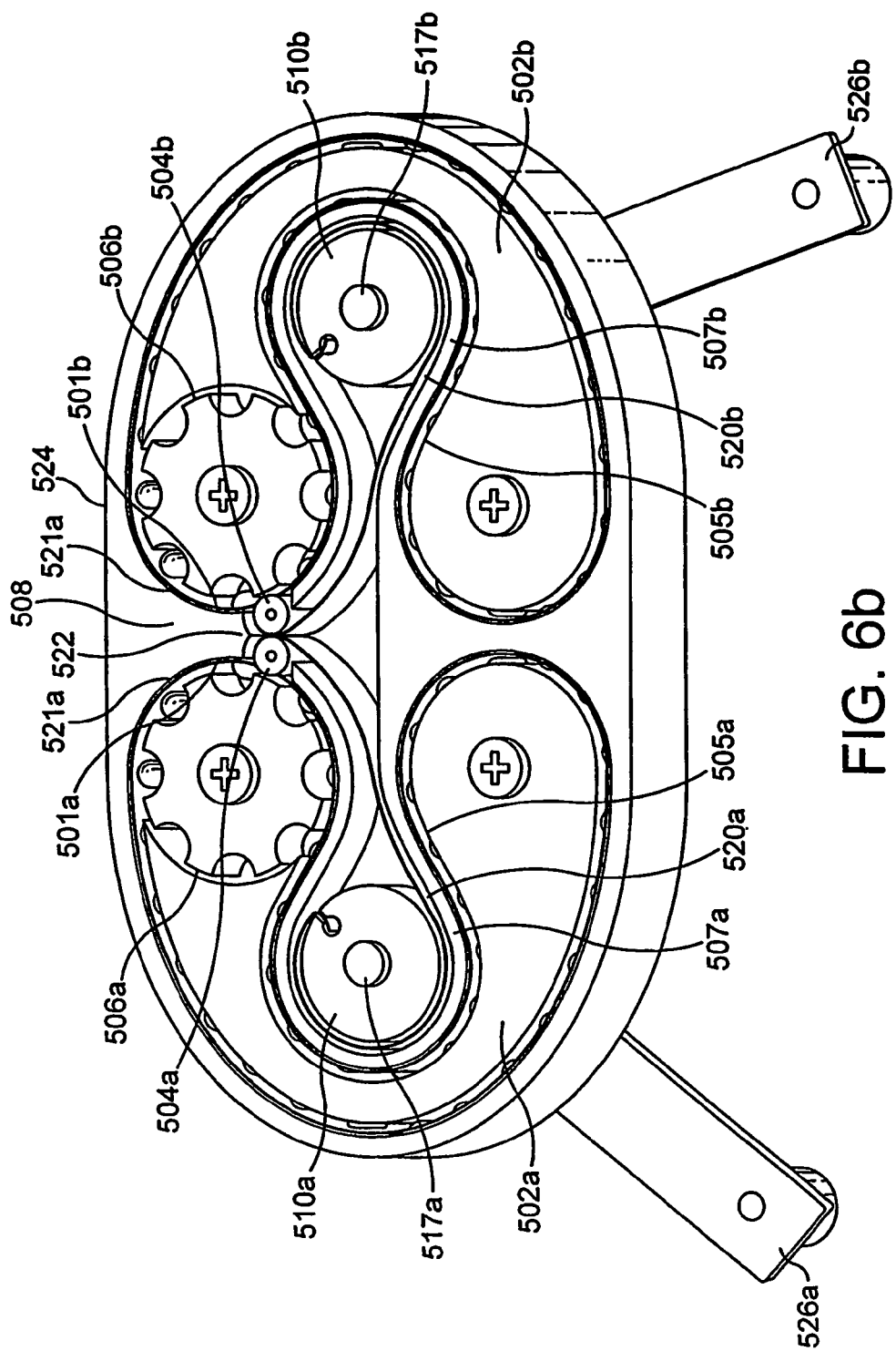

FIGS. 6a and 6b illustrate a sectional view of base unit 500 of a medicament dispenser according to the invention. It will be appreciated that the dispenser of FIGS. 6a and 6b is a variation of that shown in FIG. 5, but with the positioning of he component parts of the dispensing mechanism positioned slightly differently to accommodate generally C-shaped loops of carrier strip.

In use, a protective cover (not shown) would be provided to the base unit 500. As shown in FIG. 6b only, first and second medicament-containing blister strips 501a, 501b are positioned about left and right lobed structures 502a, 502b of the base unit 500. Each blister strip 501a, 501b (visible in FIG. 6b only) has a continuous loop form. That is to say, each strip comprises a continuous loop of base foil 521a, 521b having pockets 504a, 504b for containing medicament arranged along the majority of its length; and a strip of lid foil 520a, 520b provided to the base foil 521a, 521b to initially seal at least all of the pockets 504a, 504b. Within the dispenser the strip 501a, 501b snakes around hub walls 505a, 505b and guide walls 507a, 507b that generally act to define the shape of each loop 501a, 501b when housed in the dispenser unit 500.

Each blister strip 501a, 501b engages in respective multi-pocket index wheel 506a, 506b, and successive pockets are thereby guided towards a central opening station 508. The rotation of the index wheels 506a, 506b is optionally coupled together. At the opening station 508, the lid foil 520a, 520b and base foil 521a, 521b parts of each strip 501a, 501b are peelably separable about beak 510a, 510b. In contrast to the embodiment of FIG. 2 (for example), the resulting empty base foil 521a, 521b is not coiled up. Rather, because it is joined (in 'continuous loop' fashion) to the tail end of the strip 501a, 501b it continues to be transported through the dispenser as the strip 501a, 501b is further advanced. The need for any distinct base foil take-up chamber (e.g. see chambers 114a, 114b of FIG. 2) is thereby avoided.

The used lid foil 520a, 520b feeds over its respective beak 510a, 510b and coils about respective lid take-up spindles 516a, 516b, which also rotate to wind up lid foil 520a, 520b thereon. Each lid take-up spindle 516a, 516b is provided with a centrally located torsion spring 517a, 517b. The function of the torsion spring 517a, 517b is to ensure a roughly constant driving tension is provided to each strip 501a, 501b by its lid take-up spindle 516a, 516b over the course of each entire strip length. In particular, each torsion spring 517a, 517b acts to compensate for the variation in drive tension associated with the increase in the effective winding diameter of each lid take-up spindle 516a, 516b as used lid foil 520a, 520b gradually becomes wrapped there around. Thus, uniform indexing of each strip 501a, 501b may be maintained over the entire strip length.

In use, the dispenser is primed by actuating levers 526a, 526b located on each side of the dispenser (which in embodiments could be replaced by a common lever 526) to drivably actuate the index wheels 506a, 506b to advance each blister strip 501a, 501b, thereby causing the leading pocket 504a, 504b thereof to be peeled open. To access the contents of the opened pockets 504a, 504b, the patient then breathes in through the outlet 524. This results in negative pressure being transmitted through manifold 522 to the opened leading pocket 504a, 504b of each strip 501a, 501b at the opening station 508. This in turn, results in the medicament powder contained within each of the opened pockets 504a, 504b being drawn out through the common manifold 522 to the outlet 524 and hence to the patient as an inhaled combination medicament dose. It be appreciated that, mixing of each separately delivered component of the combined medicament product happens as the powder is transported from each opened pocket 504a, 504b to the outlet 524.

Figure 7A:
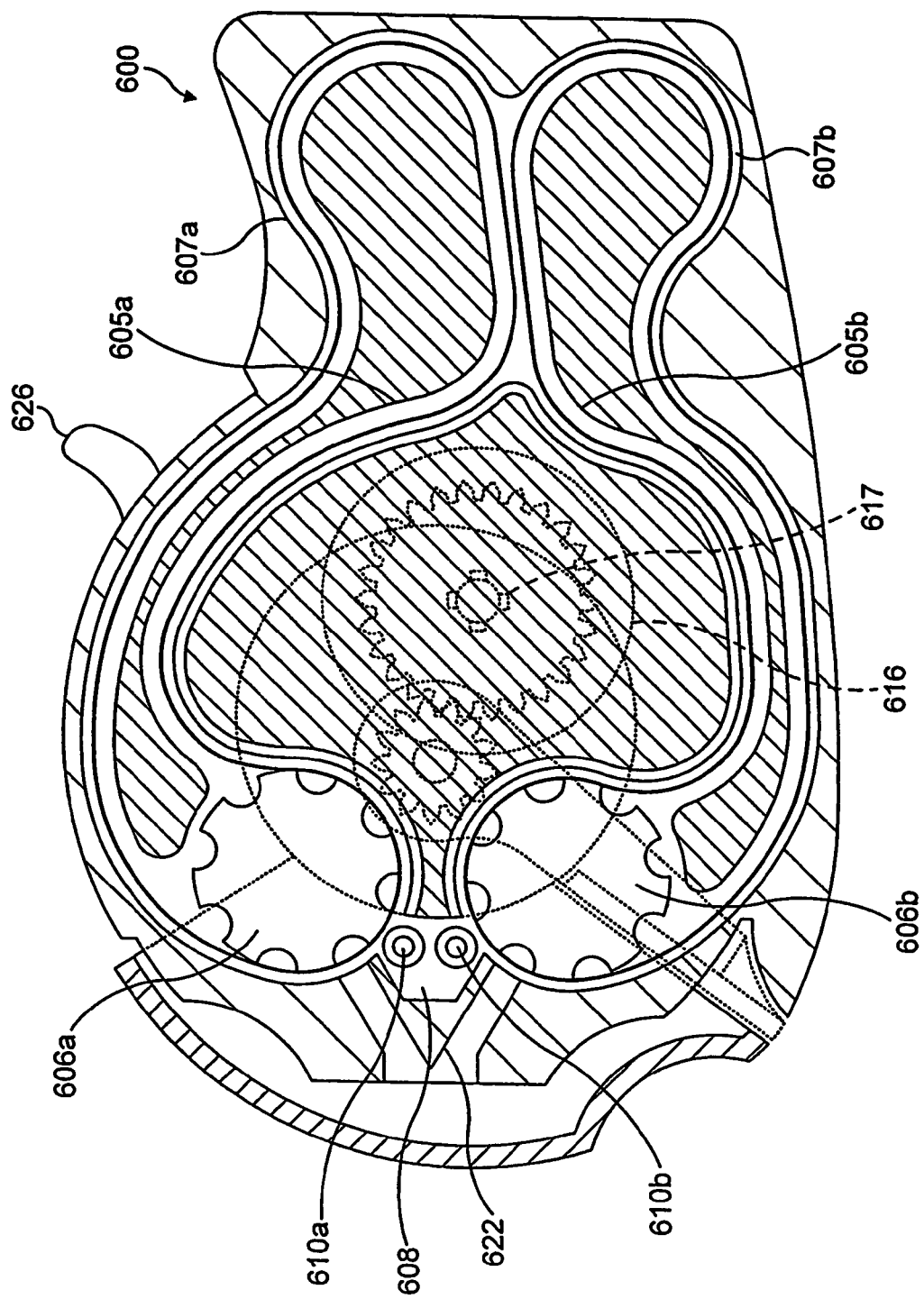
FIG. 7a shows a sectional plan view of a further medicament dispenser in accord with the invention capable of receiving medicament carriers with base sheets in continuous loop form and FIG. 7b shows a section plan view of a simplified form of the medicament dispenser of FIG. 7a with medicament carriers received thereby.
Figure 7B:
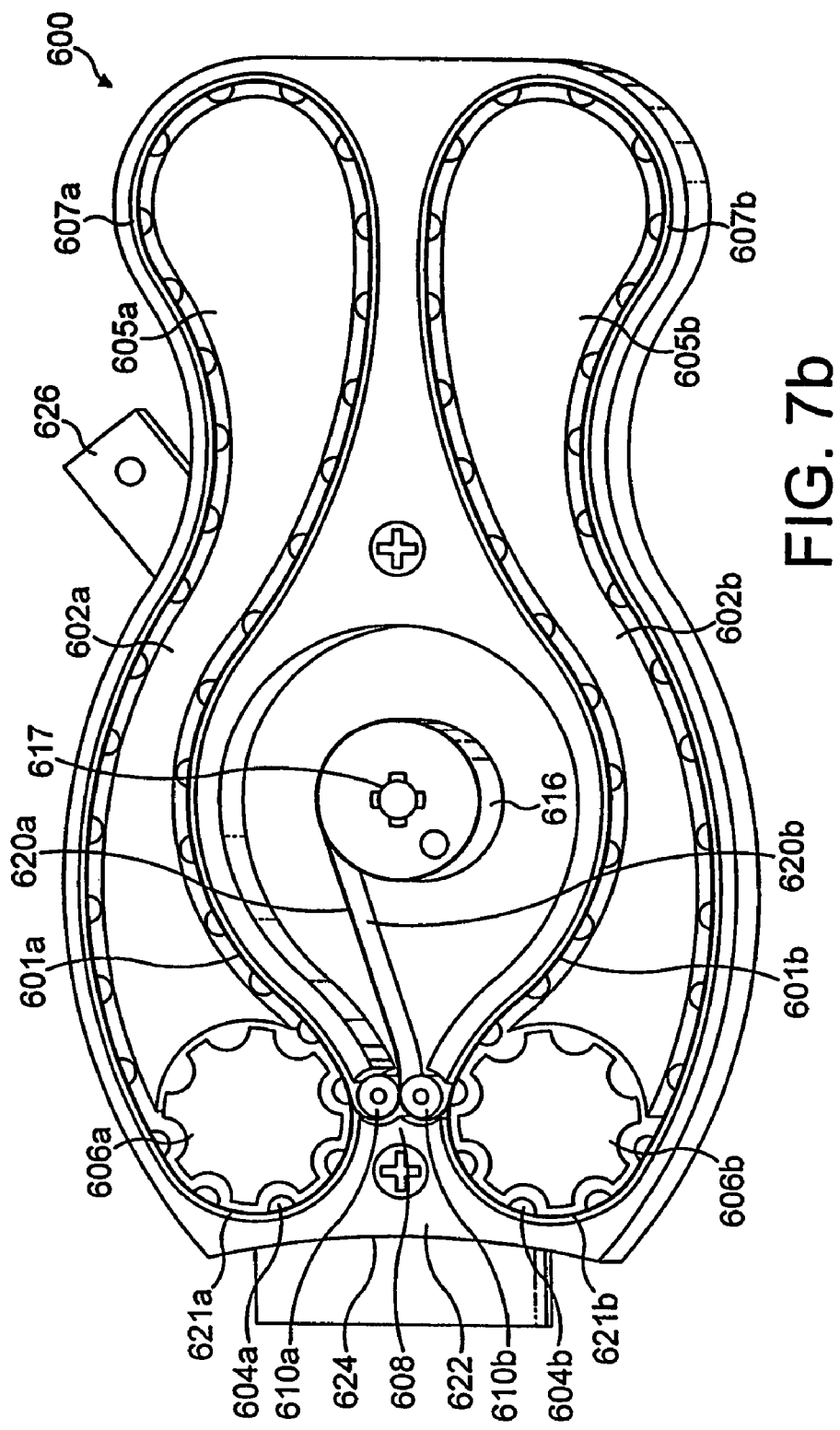

FIGS. 7a and 7b illustrate a sectional view of base unit 600 of a medicament dispenser according to the invention. It will be appreciated that the dispenser of FIGS. 7a and 7b is a variation of that shown in FIG. 5, but with a common take-up spindle and also with the positioning of the component parts of the dispensing mechanism positioned slightly differently to accommodate generally S-shaped loops of carrier strip.

In use, a protective cover (not shown) would be provided to the base unit 600. As shown in FIG. 7b only, first and second medicament-containing blister strips 601a, 601b are positioned about top and bottom S-shaped structures 602a, 602b of the base unit 600. Each blister strip 601a, 601b (visible in FIG. 7b only) has a continuous loop form. That is to say, each strip comprises a continuous loop of base foil 621a, 621b having pockets 604a, 604b for containing medicament arranged along the majority of its length; and a strip of lid foil 620a, 620b provided to the base foil 621a, 621b to initially seal at least all of the pockets 604a, 604b. Within the dispenser the strip 601a, 601b snakes around hub walls 605a, 605b and guide walls 607a, 607b that generally act to define the S-shape of each loop 601a, 601b when housed in the dispenser unit 600.

Each blister strip 601a, 601b engages in respective multi-pocket index wheel 606a, 606b, and successive pockets are thereby guided towards a central opening station 608. The rotation of the index wheels 606a, 606b is optionally coupled together. At the opening station 608, the lid foil 620a, 620b and base foil 621a, 621b parts of each strip 601a, 601b are peelably separable about beak 610a, 610b. In contrast to the embodiment of FIG. 2 (for example), the resulting empty base foil 621a, 621b is not coiled up. Rather, because it is joined (in 'continuous loop' fashion) to the tail end of the strip 601a, 601b it continues to be transported through the dispenser as the strip 601a, 601b is further advanced. The need for any distinct base foil take-up chamber (e.g. see chambers 114a, 114b of FIG. 2) is thereby avoided. The used lid foil 620a, 620b feeds over its respective beak 610a, 610b and coils about common lid take-up spindle 616, which also rotate to wind up lid foil 620a, 620b thereon. The lid take-up spindle 616 is provided with a centrally located torsion spring 617. The function of the torsion spring 617 is to ensure a roughly constant driving tension is provided to each strip 601a, 601b by lid take-up spindle 616 over the course of each entire strip length. In particular, the torsion spring 617 acts to compensate for the variation in drive tension associated with the increase in the effective winding diameter of each lid take-up spindle 616 as used lid foil 620a, 620b gradually becomes wrapped there around. Thus, uniform indexing of each strip 601a, 601b may be maintained over the entire strip length.

In use, the dispenser is primed by actuating levers 626 located on the side of the dispenser to drivably actuate the index wheels 606a, 606b to advance each blister strip 601a, 601b, thereby causing the leading pocket 604a, 604b thereof to be peeled open. To access the contents of the opened pockets 604a, 604b, the patient then breathes in through outlet 624. This results in negative pressure being transmitted through manifold 622 to the opened leading pocket 604*a*, 604*b* of each strip 601*a*, 601*b* at the opening station 608. This in turn, results in the medicament powder contained within each of the opened pockets 604*a*, 604*b* being drawn out through the common manifold 622 to the outlet 624 and hence to the patient as an inhaled combination medicament dose. It be appreciated that, mixing of each separately delivered component of the combined medicament product happens as the powder is transported from each opened pocket 604*a*, 604*b* to the outlet 624.

Figure 8A:
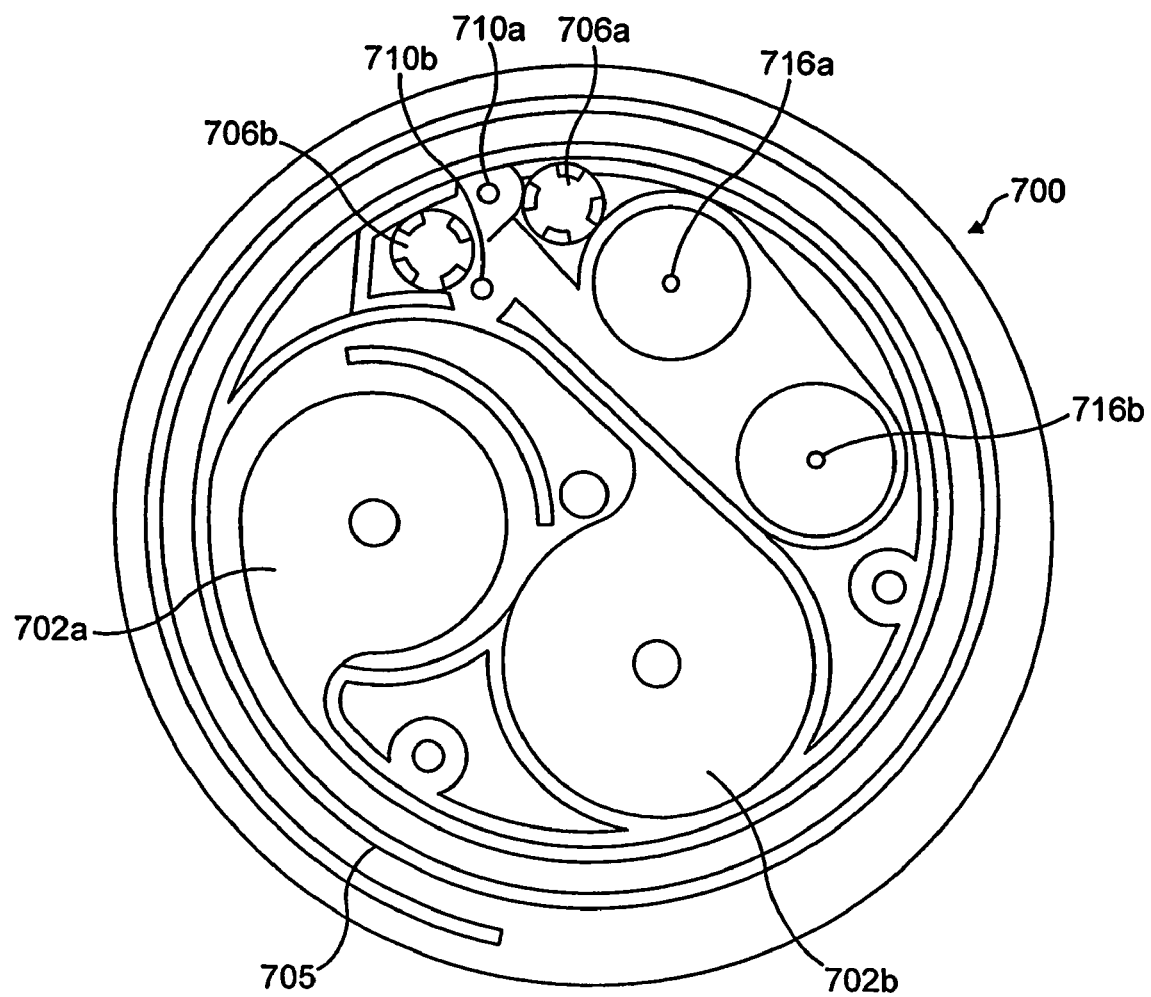
FIG. 8a shows a sectional plan view of a further medicament dispenser in accord with the invention capable of receiving medicament carriers in elongate strip form and FIG. 8b shows a section plan view of the medicament dispenser of FIG. 8a with medicament carriers received thereby.
Figure 8B:
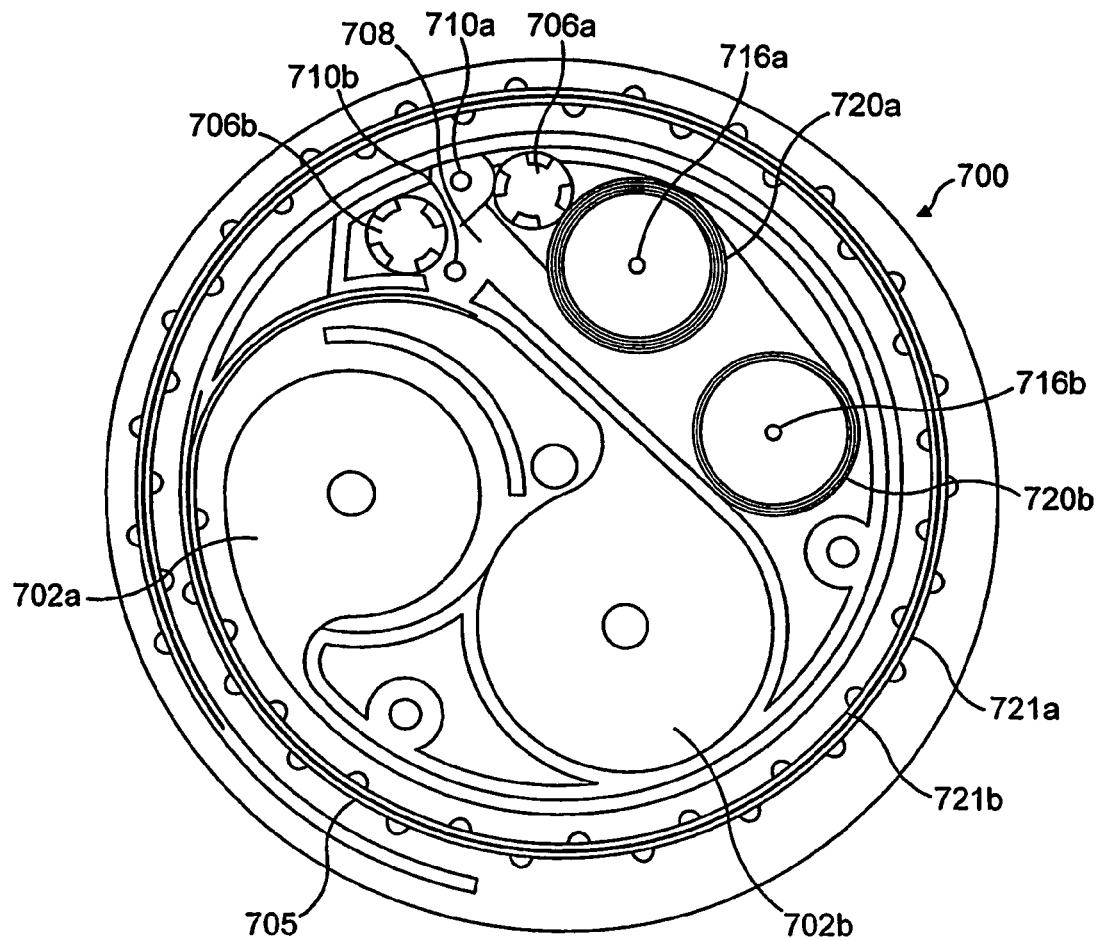

FIGS. 8*a* and 8*b* illustrate a sectional view of the dispensing mechanism of a base unit of medicament dispenser 700 according to one aspect of the invention. FIG. 8*a* shows the dispenser absent medicament carrier and FIG. 8*b* shows the dispenser containing two blister strip form medicament carriers in the 'end of life' (i.e. all medicament dispensed) configuration.

In use, a protective cover (not shown) would be provided to the base unit 700. The base unit 700 is arranged such that first and second medicament-containing blister strips initially coil up within respective first and second chambers 702*a*, 702*b* of the base unit 700. Each blister strip engages in respective multi-pocket index wheel 706*a*, 706*b*, and successive pockets are thereby guided towards a central opening station 708. The rotation of the index wheels 706*a*, 706*b* is suitably coupled together.

At the opening station 708, the lid foil 720*a*, 720*b* and base foil 721*a*, 721*b* parts of each strip are peelably separable about beak 710*a*, 710*b*. The resulting 'Waste' base foil 721*a*, 721*b* is directed towards spiral-shaped track 705, which accommodates the 'waste' base foil 721*a*, 721*b* in relative back-to-back alignment. As shown in FIG. 8*b*, the 'waste' base foils 721*a*, 721*b* are therefore stowed in a spiral configuration (whose shape is defined by the spiral track 705) that locates at the periphery of the dispensing mechanism.

The used lid foil 720*a*, 720*b* feeds over its respective beak 710*a*, 710*b* and coils about its lid take-up spindle 716*a*, 716*b* (which is also rotatable). The lid take-up spindle 716*a*, 716*b* generally takes the form of a torsion hub.

In use, the dispenser is primed by drivably actuating the index wheels 706*a*, 706*b* and lid-take up spindles 716*a*, 716*b* to advance each blister strip thereby causing the leading pocket thereof to be peeled open. To access the contents of the opened pockets the patient then breathes in through an outlet (not visible). This results in negative pressure being transmitted through manifold (not visible) to the opened leading pocket of each strip at the opening station 708. This in turn, results in the medicament powder contained within each of the opened pockets being drawn out through the manifold to the outlet and hence to the patient as an inhaled combination medicament dose. It be appreciated that, mixing of each separately delivered component of the combined medicament product happens as the powder is transported from each opened pocket to the outlet.

FIG. 9 illustrates a schematic view of dispensing mechanism 800 of a medicament dispenser according to the invention. In use, the mechanism would be enclosed within a device housing defining a mouthpiece outlet.

As shown, first and second medicament-containing blister strips 801*a*, 801*b* are positioned in 'caterpillar track arrangement' about respective multi-pocket index wheels 806*a*, 806*b* and free-running rollers 805*a*, 805*b*. Each blister strip 801*a*, 801*b* has a continuous loop form. That is to say, each strip comprises a continuous loop of base foil 821*a*, 821*b* having pockets 804*a*, 804*b* for containing medicament regularly spaced there along; and a strip of lid foil 820*a*, 820*b* provided to the base foil 821*a*, 821*b* to initially seal at least all of the pockets 804*a*, 804*b*. The two index wheels 806*a*, 806*b* are arranged to rotate in mutually opposing directions (i.e. one clockwise, the other anti-clockwise) such that within the dispenser the two strip 801*a*, 801*b* travel in a mutually opposing rotary sense.

Each blister strip 801*a*, 801*b* engages in respective multi-pocket index wheel 806*a*, 806*b*, and successive pockets are thereby guided towards a central opening station 808. The rotation of the index wheels 806*a*, 806*b* is coupled together. At the opening station 808, the lid foil 820*a*, 820*b* and base foil 821*a*, 821*b* parts of each loop 801*a*, 801*b* are peelably separable about beak 810*a*, 810*b*. The resulting empty base foil 821*a*, 821*b* continues to be transported through the dispenser as the continuous loop form strip 801*a*, 801*b* is further advanced. The need for any distinct base foil take-up chamber (e.g. see chambers 114*a*, 114*b* of FIG. 2) is thereby avoided.

The leading end of the lid foil 820*a*, 820*b* of each strip 801*a*, 801*b* may be seen to be joined at join point 830*a*, 830*b* to the base sheet 821*b*, 821*a* of the other strip. The effect of this joining is that as each strip 801*a*, 801*b* is rotated about its index wheel 806*a*, 806*b* it results in the lid foil 820*b*, 820*a* of the other strip being pulled over its respective beak 810*b*, 810*a* to peelably separate the lid foil 820*b*, 820*a* from the base sheet 821*b*, 821*a* of that other strip 801*b*, 801*a* and open the leading pocket 804*b*, 804*a* thereof. As the strip 801*a*, 801*b* is further rotated about its index wheel 806*a*, 806*b* (e.g. as a result of subsequent pocket-opening operations) the detached (i.e. 'waste') lid foil 820*b*, 820*a* tends to associate (e.g. cling to) the base sheet 821*a*, 821*b* of the other strip to which its end is joined. It will be appreciated that this arrangement negates the need for any particular 'waste' lid foil collecting area or component part to be provided to the dispenser, thereby saving space.

In use therefore, the dispenser is primed by drivably actuating the index wheels 06*a*, 806*b* to advance each blister strip 801*a*, 801*b*, thereby causing the leading pocket 804*a*, 804*b* thereof to be peeled open. An appropriate ratchet mechanism is employed to ensure that in each actuating movement, each blister strip 801*a*, 801*b* is only moved sufficiently to open one pocket 804*a*, 804*b* thereof. To access the contents of the opened pockets 804*a*, 804*b*, the patient then breathes in through an outlet (not shown). This results in negative pressure being transmitted through manifold 822 to the opened leading pocket 804*a*, 804*b* of each strip 801*a*, 801*b* at the opening station 808. This in turn, results in the medicament powder contained within each of the opened pockets 804*a*, 804*b* being drawn out through the common manifold 822 to the outlet (not shown) and hence to the patient as an inhaled combination medicament dose. It be appreciated that, mixing of each separately delivered component of the combined medicament product happens as the powder is transported from each opened pocket 804*a*, 804*b* to the outlet 824.

Figure 10:
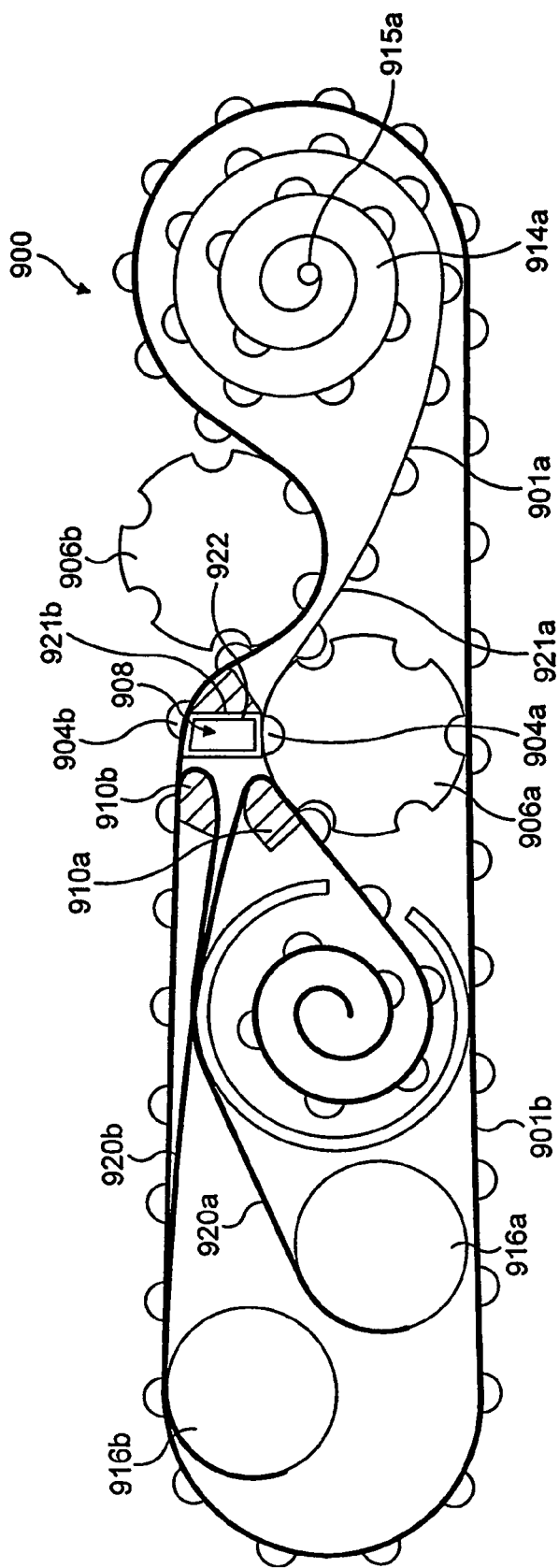

FIG. 10 illustrates a schematic view of dispensing mechanism 900 of a medicament dispenser according to the invention. In use, the mechanism would be enclosed within a device housing defining a mouthpiece outlet. It will be appreciated from the detailed description below that the mechanism is a 'hybrid' dispensing mechanism suitable for use with a medicament carrier in blister strip form that nestles within a second medicament carrier in continuous loop form.

First medicament carrier 901*a* is in strip form and second medicament carrier is in continuous loop form 901*b*, each comprising blisters spaced regularly there along. Each medicament carrier 901*a*, 901*b* engages in respective multi-pocket index wheel 906*a*, 906*b*, and successive blister pockets are thereby guided towards a central opening station 908. The rotation of the index wheels 906*a*, 906*b* is coupled together.

At the opening station 908, the lid foil 920a, 920b and base foil 921a, 921b parts of each strip 901a, 901b are peelably separable about beak 910a, 910b.

The resulting 'waste' base foil 921a of the strip form carrier 901a coils up in base take-up chamber 914a. Rotatable base foil anchor spindle 915a anchors the end of the base foil 921a in the chamber 914a. Progressive rotation of the anchor spindle 915a results in the 'waste' base foil 921a being wound up there around into a tight coil. Typically, the rotation of the base spindle 915a is coupled to that of its index wheel 906a. The 'waste' lid foil 920a of the strip form carrier 901a feeds over its respective beak 910a and coils about its lid take-up spindle 916a.

The resulting 'waste' base foil 921b of the continuous loop form carrier 901b is not coiled up. Rather, because it joins (in 'continuous loop' fashion) to the tail end of the strip 901b it continues to be transported through the dispenser, as the strip 901b is further advanced. The need for any distinct base foil take-up spindle is thereby avoided. The 'waste' lid foil 920b of the continuous loop form carrier 901b feeds over its respective beak 910b and coils about its lid take-up spindle 916b.

In use, the dispenser is primed by drivably rotating both respective index wheels 906a, 906b and lid-take up spindles 916a, 916b to advance each medicament carrier 901a, 901b, thereby causing the leading pocket 904a, 904b thereof to be peeled open. To access the contents of the opened pockets 904a, 904b, the patient then breathes in through an outlet (not shown). This results in negative pressure being transmitted through common manifold 922 to the opened leading pocket 904a, 904b of each strip 901a, 901b at the opening station 908. This in turn, results in the medicament powder contained within each of the opened pockets 904a, 904b being drawn out through the common manifold 922 to the outlet 924 and hence to the patient as an inhaled combination medicament dose. It be appreciated that, mixing of each separately delivered component of the combined medicament product happens as the powder is transported from each opened pocket 904a, 904b to the outlet 924.

Figure 11:
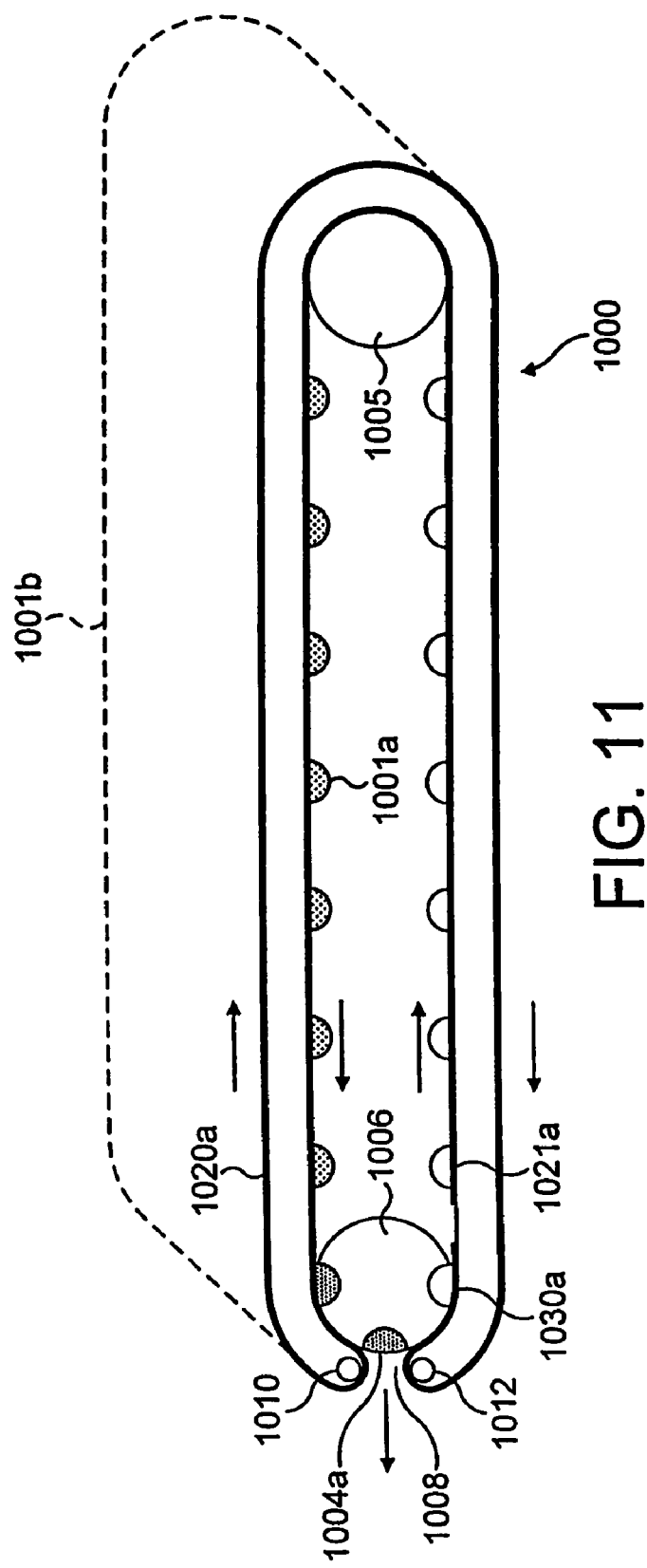
FIG. 11 shows schematic cutaway view of a further medicament dispenser in accord with the invention.

FIG. 11 illustrates a schematic view of dispensing mechanism 1000 of a medicament dispenser according to the invention. In use, the mechanism would be enclosed within a device housing defining a mouthpiece outlet.

First 1001a and second 1001b medicament-containing blister strips are positioned in 'caterpillar track arrangement'. As drawn, only the details of the first medicament-containing blister strip 1001a are visible, but it will be appreciated that the second strip 1001b mirrors its form and layout.

The first medicament-containing blister strip 1001a is retained caterpillar-like by multi-pocket index wheel 1006 and free-running roller 1005. The blister strip 1001a has a continuous loop form. That is to say, it comprises a continuous loop of base to foil 1021a having pockets 1004a for containing medicament regularly spaced there along; and a strip of lid foil 1020a provided to the base foil 1021a to initially seal at least all of the pockets 1004a.

The blister strip 1001a engages in respective multi-pocket index wheel 1006 and by rotation thereof successive pockets are thereby guided towards a central opening station 1008. At the opening station 1008, the lid foil 1020a and base foil 1021a parts of the loop 1001a are peelably separable about beak 1010. The resulting empty base foil 1021a continues to be transported through the dispenser as the continuous loop form strip 1001a is further advanced. The need for any distinct base foil take-up chamber (e.g. see chambers 114a, 114b of FIG. 2) is thereby avoided.

The leading end of the lid foil 1020a of the strip 1001a may be seen to be looped back over the end roller 1005, then over opposing beak 1012 and finally joined at join point 1030a to its base sheet 1021a of the strip 1001a. The effect of this 'doubling-back' of the lid foil 1020a and joining to the base sheet 1021a as shown, is that as the strip 1001a is rotated about its index wheel 1006a the leading end of lid foil 1020a is pulled further over opposing beak 1012, transmitting pulling force through the lid foil 1020a via end roller 1005 and then beak 1010 to peelably separate the lid foil 1020a from the base sheet 1021a of the strip 1001a, and open the leading pocket 1004a thereof. As the strip 1001a is further rotated about its index wheel 1006a (e.g. as a result of subsequent pocket-opening operations) the detached (i.e. 'waste') lid foil 1020a tends to be retained in looped position around the end roller 1005 and opposing beak 1012 and ultimately pulled towards the 'waste' base sheet 1021a to which its end is joined. It will be appreciated that this arrangement negates the need for any particular 'waste' lid foil collecting area or component part to be provided to the dispenser, thereby saving space.

In use therefore, the dispenser is primed by drivably actuating the index wheels 1006a to advance each blister strip 1001a thereby causing the leading pocket 1004a thereof to be peeled open. An appropriate ratchet mechanism is employed to ensure that in each actuating movement, each blister strip 1001a is only moved sufficiently to open one pocket 1004a thereof. To access the contents of the opened pockets 1004a the patient then breathes in through an outlet (not shown). This results in negative pressure being transmitted through manifold (not shown) to the opened leading pocket 1004a of each strip 1001a at the opening station 1008. This in turn, results in the medicament powder contained within each of the opened pockets 1004a being drawn out through the common manifold to the outlet (not shown) and hence to the patient as an inhaled combination medicament dose. It be appreciated that, mixing of each separately delivered component of the combined medicament product happens as the powder is transported from each opened pocket 1004a to the outlet.

FIG. 12a shows a side view of a continuous loop form medicament carrier 1101a, 1101b arrangement suitable for use in fold-up configuration, as shown in FIG. 12b. FIG. 12c shows a medicament dispenser 1100 for receiving the foldable carrier configuration of FIG. 12b.

Referring now to FIGS. 12a and 12b, first and second medicament-containing blister strips 1101a, 1101b are retained in side-by-side 'caterpillar track arrangement' by end-located, common multi-pocket index wheels 1105, 1106 (e.g. 6 mm index wheels). Each blister strip 1101a, 1101b has a continuous loop form. That is to say, each strip comprises a continuous loop of base foil having pockets 1104a for containing medicament regularly spaced there along; and a strip of lid foil provided to the base foil to initially seal at least all of the pockets 1104a. The two, end-located common index wheels 1105, 1106 are arranged for co-rotation (i.e. in the same direction) about respective axles 1135, 1136 such that within the dispenser 1100 the two strips 1101a, 1101b travel in a coupled sense.

Referring to FIG. 12b, it may be seen that the strips 1101a, 1101b may be arranged in fold-up configuration for receipt by the dispenser 1100. Such configuration has the advantage of being extremely compact.

Referring now to FIG. 12c, the dispenser 1100 may be seen to comprise first 1140 and second 1141 casing units rotatably coupled at pivot 1142 to form a flip-out form casing readily movable between flipped open and closed positions. The second casing unit 1141 is provided with outlet 1124 for delivery of released powder form medicament to an orifice of the patient. In variations, the outlet 1124 is shaped as a mouthpiece or as a nozzle for receipt by the nasal cavity of a patient.

The dispenser 1100 is arranged to receive the medicament carrier strips 1101a, 1101b, as shown. Thus, common index wheels 1105, 1106 are pivotally mounted for rotation within the respective first 1140 and second 1141 casing units such that the medicament carrier strips 1101a, 1101b may be transported within the dispenser 1100. As shown in FIG. 12c, the dispenser 1100 is in the flipped open configuration, but when closed it will be appreciated that the strips 1101a, 1101b adopt the compact, fold-up configuration as shown in FIG. 12b.

The dispenser 1100 is also provided with means to index and access medicament from each blister strip 1101a, 1101b to enable the delivery of a combination medicament product. Thus, each loop-form blister strip 1101a, 1101b may be advanced by rotation of the common, multi-pocket index wheels 1105, 1106 to bring successive pockets 1104a thereof towards a central opening station 1108. At the opening station 1108, the lid foil and base foil parts of each loop 1101a, 1101b are peelably separable about a peel surface (not visible). The resulting empty base foil continues to be transported through the dispenser as the continuous loop form strip 1101a, 1101b is further advanced. The need for any distinct base foil take-up chamber is thereby avoided.

The used lid foil feeds over the peel surface and is coiled about common, lid foil take-up spindle 1116 which rotates to wind up lid foil 1120a, 1120b thereon. The lid take-up spindle 1116 is provided with a centrally located torsion spring 1117. The function of the torsion spring 1117 is to ensure a roughly constant driving tension is provided to each strip 1101a, 1101b by the common lid take-up spindle 1116 over the course of each entire strip length. In particular, the torsion spring 1117 acts to compensate for the variation in drive tension associated with the increase in the effective winding diameter of common lid take-up spindle 1116 as used lid foil 1120a, 1120b gradually becomes wrapped there around. Thus, uniform indexing of each strip 1101a, 1101b may be maintained over the entire loop form.

In use therefore, the dispenser 1100 is primed by drivably actuating the index wheels 1105, 1106 to advance both blister strips 1101a, 1101b, thereby causing the leading pocket 1104a, 1104b thereof to be peeled open. An appropriate ratchet mechanism may be employed to ensure that in each actuating movement, each blister strip 1101a, 1101b is only moved sufficiently to open one pocket 1104a, 1104b thereof. To access the contents of the opened pockets 1104a, 1104b, the patient then breathes in through the outlet 1124. This results in negative pressure being transmitted through suitable air channelling means (not visible) to the opened leading pocket 1104a, 1104b of each strip 1101a, 1101b at the opening station 1108. This in turn, results in the medicament powder contained within each of the opened pockets 1104a, 1104b being drawn out through the air channelling means to the outlet 1124 and hence to the patient as an inhaled combination medicament dose. It be appreciated that, mixing of each separately delivered component of the combined medicament product happens as the powder is transported from each opened pocket 1104a, 1104b to the outlet 1124.

In a variation herein, the dispenser 1100 is provided with means to supply pressurized air to the open pockets 1104a, 1104b to assist in aerosolisation of the medicament powder contained therein. Such means may for example, comprise an air pump or an aerosol canister filled with compressed air.

Figure 13:
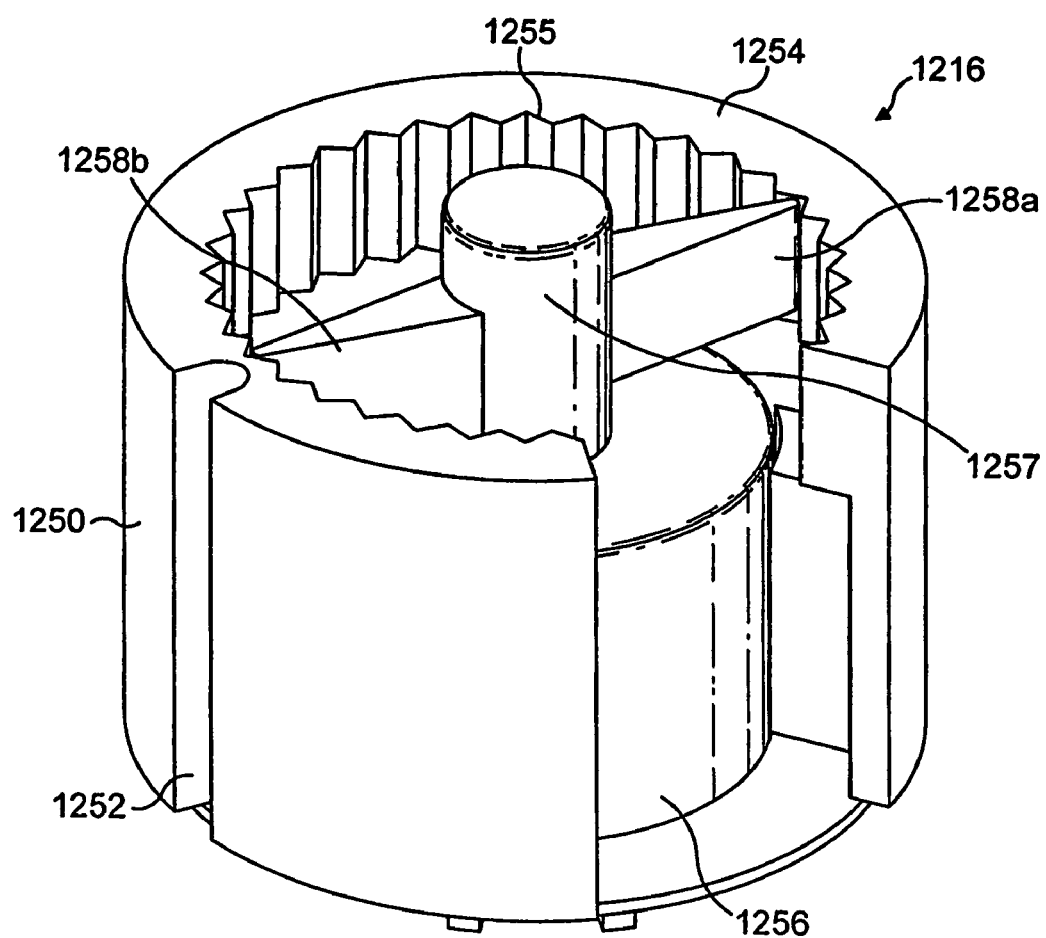
FIG. 13 shows a perspective view of a lid driver suitable for use with medicament dispensers herein.

FIG. 13 shows a vane hub form lid driver 1216, which may be used in any of the dispensers of FIGS. 2 to 12c, as an alternative to the form of lid driver illustrated therein.

The lid driver 1216 comprises a rigid outer drum 1250 having a lateral indent 1252 for attachment of lid foil (not shown) provided thereto. The inner wall 1254 of the drum 1250 is provided with multiple teeth 1255. Insert 1256 locates within the drum 1250 and defines spindle 1257 and vane arms 1258a, 1258b, the ends of which normally interact with teeth 1255 on the inner wall 1254 of the drum 1250. The insert 1256 is rotatable relative to the drum 1256, but that rotation only occurs when sufficient rotational force is applied to the drum 1256 to overcome the interaction of the teeth 1255 with the respective, resiliently flexible vane arms 1258a, 1258b. The nature of this interaction therefore defines a slipping (i.e. clutch) force, which must be overcome for free rotation of the insert 1256 relative to the drum 1250 to occur. In the absence of the slipping force the drum 1250 and insert 1256 are fixed relative to each other and rotatable as a single unit.

In use, the end of a lid foil of a peelable blister strip form medicament carrier (e.g. as shown in FIG. 1) is attached to attachment point 1252. The drum 1250 is then rotated to wind up lid foil thereon and to cause peeling open of the medicament carrier (e.g. as described by reference to the earlier Figures). In more detail, the drum 1250 and insert 1256 therein initially rotate as a single unit, lid foil gradually becomes wrapped around the drum 1250, and overall the lid driver 1216 provides driving force to peel lid foil from base foil of the medicament carrier. When that driving force exceeds a certain level (i.e. the slipping force) the interaction of the vane arms 1258a, 1258b and the teeth 1255 result in slippage and the insert 1256 is caused to rotate relative to the drum 1250, thereby preventing excess driving force from being transferred to the lid foil.

It will therefore be appreciated that the function of the insert 1256 is to prevent transfer of excess drive force to the lid foil by the drum 1250 of the lid driver 1216. In particular, the slipping of insert 1256 relative to drum 1250 once a slipping force is exceeded acts to compensate for the variation in drive tension associated with the increase in the effective winding diameter of common lid take-up spindle 1216 as used lid foil gradually becomes wrapped around the drum 1250. Thus, uniform indexing of each strip may be maintained over the entire strip length.

Figure 14A:
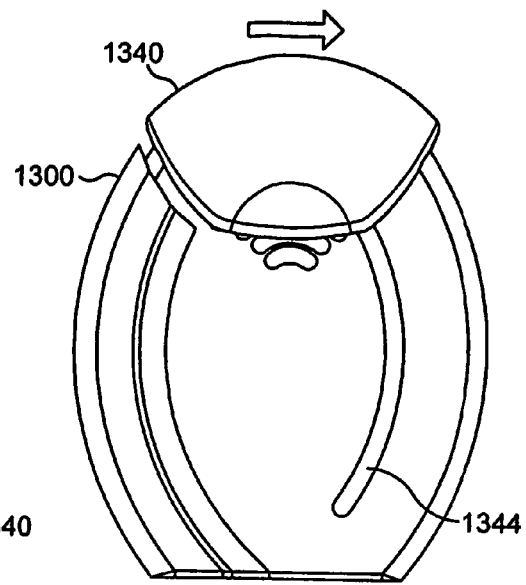
FIGS. 14a to 14c show side views of a medicament dispenser herein with a movable cover drive mechanism at different stages of the cover drive action.
Figure 14B:
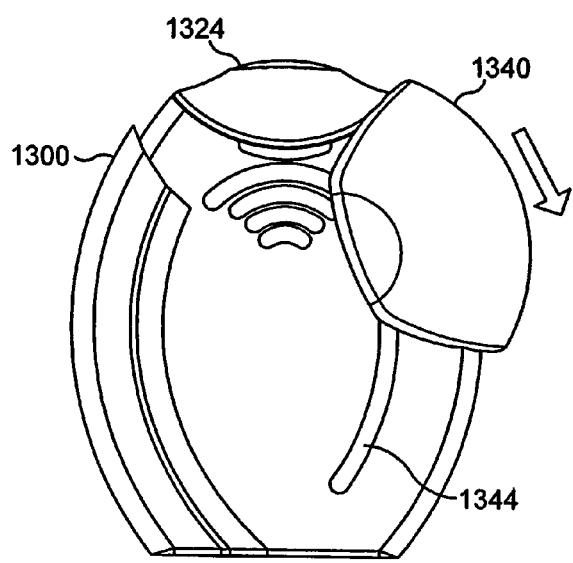
Figure 14C:
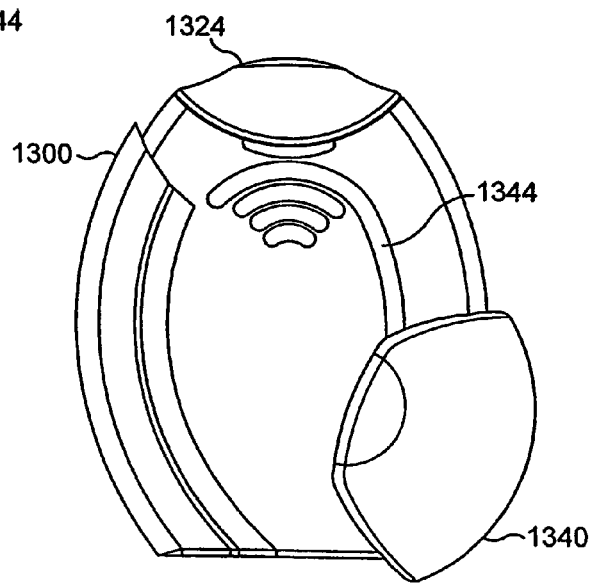
Figure 15:
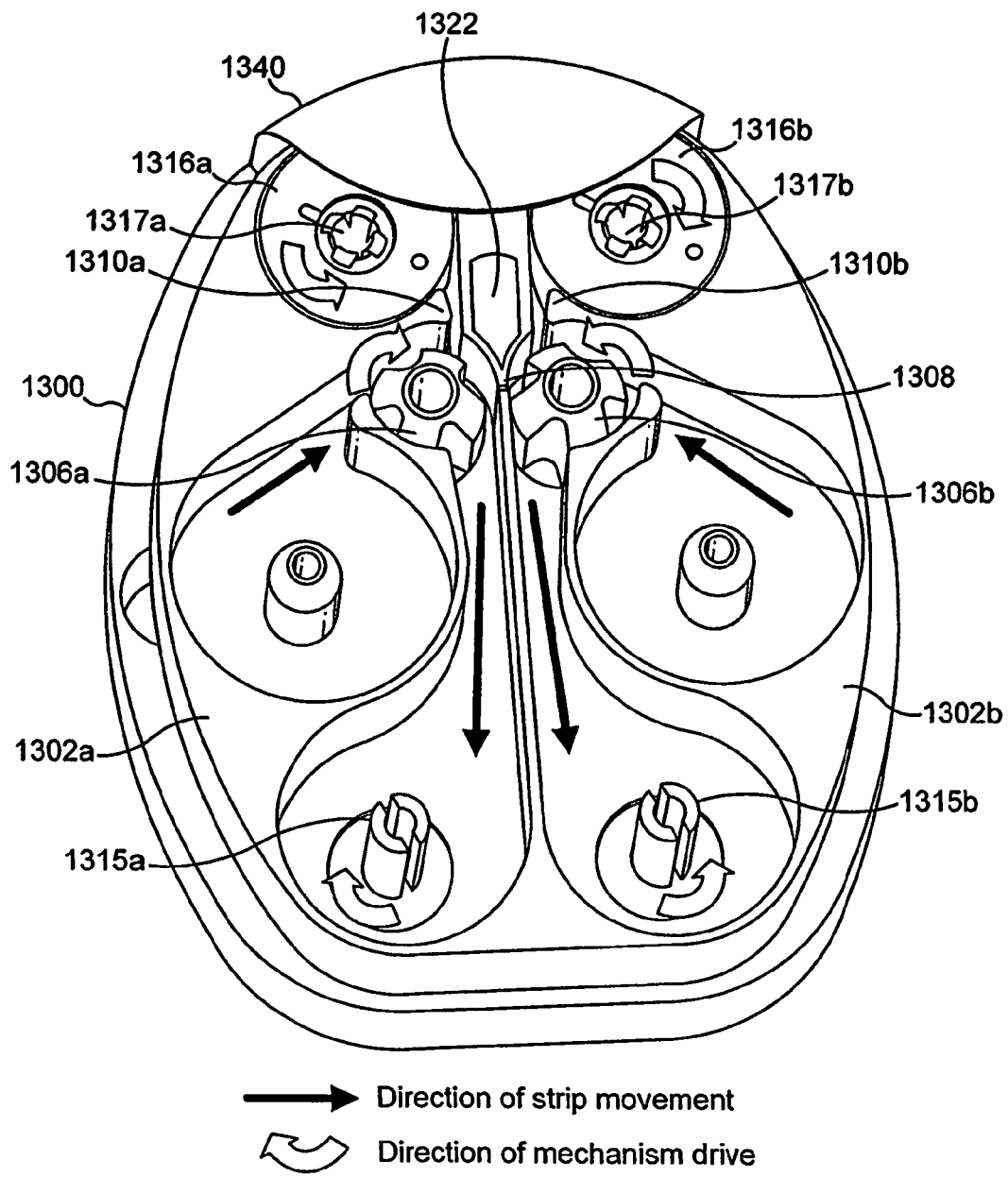
FIG. 15 shows a perspective view of the inner workings of the medicament dispenser of FIGS. 14a to 14c.

FIGS. 14a to 14c show side external views of a medicament dispenser herein with a movable cover 1340 at different stages of the cover drive action. FIG. 15 shows a perspective view of the inner workings of the medicament dispenser of FIGS. 14a to 14c, which are actuable in response to movement of the cover 1340.

Movable cover 1340 is provided to the base unit 1300 and acts as the drive mechanism for the parts of the dispensing mechanism and blister strips (not shown) contained there within. In the 'at rest' position, as shown in FIG. 14a, the movable cover 1340 is positioned such as to cover mouthpiece 1324. It may be seen that the cover 1340 is movable along track 1344 from 'at rest' (FIG. 14a) to 'primed' (FIG. 14b) to 'actuated' (FIG. 14c) positions. As will become clear from the detailed description below, such movement of the cover 1340 is coupled via gearing (not shown) to the strip advancement mechanism of the dispenser to prime and actuate the dispenser for the delivery of medicament.

Respective left and right chambers 1302a, 1302b of the base unit 1300 are arranged for receipt of first and second medicament-containing blister strips (not shown, but having the form of the strip of FIG. 1). In use, each blister strip engages in its respective four pocket index wheel 1306a, 1306b, and successive pockets are thereby guided towards a central opening station 1308. At the opening station 1308, the lid foil and base foil parts of each strip are peelably separable about beak 1310a, 1310b. The resulting empty base foil coils wind up in a tight coil on respective base take-up spools 1315a, 1315b, which rotate as shown.

Used lid foil feeds over its respective beak 1310a, 1310b and coils about respective lid take-up spindles 1316a, 1316b, which also rotate as shown to wind up lid foil thereon. Each lid take-up spindle 1316a, 1316b is provided with a centrally located torsion spring 1317a, 1317b. The function of the torsion spring 1317a, 1317b is to ensure a roughly constant driving tension is provided to each strip by its lid take-up spindle 1316a, 1316b over the course of each entire strip length. In particular, each torsion spring 1317a, 1317b acts to compensate for the variation in drive tension associated with the increase in the effective winding diameter of each lid take-up spindle 1316a, 1316b as used lid foil gradually becomes wrapped there around. Thus, uniform indexing of each strip is maintained over the entire strip length.

In use, the dispenser is actuated by the movement of movable cover 1340 along track 1344 to drivably rotate the index wheels 1306a, 1306b and lid-take up spindles 1316a, 1316b to advance each blister strip. The movement of the cover 1340 is coupled to that of the index wheels 1306a, 1306b and lid-take up spindles 1316a, 1316b by suitable gearing (not visible). The gearing is arranged such that movement of the cover from the 'at rest' (FIG. 14a) to 'primed' (FIG. 14b) position does not itself result in any rotation of the index wheels 1306a, 1306b and lid-take up spindles 1316a, 1316b, but further movement to the 'actuated' (FIG. 14c) results in sufficient rotation to advance each blister strip by one pocket distance.

Advancement of each strip causes the leading pocket thereof to be peeled open and brought into communication with manifold 1322, which itself communicates with mouthpiece 1324. Since the inner workings and blister strips of the dispenser 1300 are comprised within a sealed housing only the leading pockets of each strip communicate with manifold 1322 and thence to the outside environment via the mouthpiece 1324.

To access the medicament contents of the opened pockets of each respective blister strip the patient breathes in through the outlet 1324. This results in air being drawn into the manifold 1322, and that air being through manifold 1322 to the opened leading pocket of each strip at the opening station 1308. In turn, this results in the medicament powder contained within each of the opened pockets being aerosolised and guided through the common manifold 1322 to the outlet 1324 and hence to the patient as an inhaled combination medicament dose.

It may be appreciated that any of the parts of the dispenser or cassette that contact the medicament suspension may be coated with materials such as fluoropolymer materials (e.g. PTFE or FEP) which reduce the tendency of medicament to adhere thereto. Any movable parts may also have coatings applied thereto that enhance their desired movement characteristics. Frictional coatings may therefore be applied to enhance frictional contact and lubricants (e.g. silicone oil) used to reduce frictional contact as necessary.

The medicament dispenser device of the invention is particularly suitable for dispensing 'multi-active' medicament combinations, particularly for the treatment of respiratory disorders such as asthma and chronic obstructive pulmonary disease (COPD), bronchitis and chest infections.

The overall 'multi-active' combination product typically comprises in combination, a first medicament comprised within a first elongate form medicament carrier; and at least one further medicament comprised within at least one further elongate form medicament carrier. The medicament dispenser device herein enables the delivery of these medicament components together in combination, even though on containment within the device they are contained within separate medicament carriers.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketobifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the diproplonate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Suitable medicament components of the overall 'multi-active' combination product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other $\beta_2$-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, INOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

Suitable PDE4 inhibitors include those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Most suitable are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other suitable medicament compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D4418 from Chiroscience and Schering-Plough; a benzodiazepine PDE4 inhibitor identified as Cl-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3, 4,4a,10b-hexahydro-8-methoxy-2-methylbenzo[c][1,6] naphthyridin-6-yl]-N,N-diisopropylbenzamide which is a mixed PDE3/PDE4 inhibitor which has been prepared and published on by Byk-Gulden, now Aitana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Suitable anticholinergic agents are those compounds that act as antagonists at the muscarinic receptor, in particular those compounds, which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines.

Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Particularly suitable anti-histamines include methapyrilene and loratadine.

Co-formulation compatibility is generally determined on an experimental basis by known methods and may depend on chosen type of medicament dispenser action.

The at least three active medicament components are suitably selected from the group consisting of anti-inflammatory agents (for example a corticosteroid or an NSAID), anticholinergic agents (for example, an $M_1$, $M_2$, $M_1/M_2$ or $M_3$ receptor antagonist), other $\beta_2$-radrenoreceptor agonists, antiinfective agents (e.g. an antibiotic or an antiviral), and antihistamines. All suitable combinations are envisaged.

Suitably, the co-formulation compatible components comprise a $\beta_2$-adrenoreceptor agonist and a corticosteroid; and the co-formulation incompatible component comprises a PDE-4 inhibitor, an anti-cholinergic or a mixture thereof. The $\beta_2$-adrenoreceptor agonists may for example be salbutamol (e.g., as the free base or the sulphate salt) or salmeterol (e.g., as the xinafoate salt) or formoterol (eg as the fumarate salt). The corticosteroid may for example, be a beclomethasone ester (e.g., the diproplonate) or a fluticasone ester (e.g., the propionate) or budesonide.

In one example, the co-formulation compatible components comprise fluticasone propionate and salmeterol, or a salt thereof (particularly the xinafoate salt) and the co-formulation incompatible component comprises a PDE-4 inhibitor, an anti-cholinergic (e.g. ipratropium bromide or tiotropium bromide) or a mixture thereof.

In another example, the co-formulation compatible components comprise budesonide and formoterol (e.g. as the fumarate salt) and the co-formulation incompatible component comprises a PDE-4 inhibitor, an anti-cholinergic (e.g. ipratropium bromide or tiotropium bromide) or a mixture thereof.

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

The medicament dispenser device of the invention is in one aspect suitable for dispensing medicament for the treatment of respiratory disorders such as disorders of the lungs and bronchial tracts including asthma and chronic obstructive pulmonary disorder (COPD). In another aspect, the invention is suitable for dispensing medicament for the treatment of a condition requiring treatment by the systemic circulation of medicament, for example migraine, diabetes, pain relief e.g. inhaled morphine.

Accordingly, there is provided the use of a device according to the invention for the treatment of a respiratory disorder, such as asthma and COPD. Alternatively, the present invention provides a method of treating a respiratory disorder such as, for example, asthma and COPD, which comprises administration by inhalation of an effective amount of medicament product as herein described from a device of the present invention.

The amount of any particular medicament compound or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The medicaments for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A medicament dispenser for containing plural elongate form medicament carriers, each medicament carrier having multiple distinct medicament dose portions carried thereby, said dispenser having a housing, and within said housing a dispensing mechanism for dispensing the distinct medicament dose portions carried by each of said plural medicament carriers, said mechanism comprising, a) at least one receiving station for receiving each of the plural medicament carriers;

b) a release for releasing in combination a distinct medicament dose portion from each of the plural medicament carriers on receipt thereof by said receiving station;
c) an outlet, positioned to be in communication with the distinct medicament dose portions releasable by said release; and
d) at least one indexer for individually indexing the distinct medicament dose portions of each of the plural medicament carriers, wherein said dispenser further comprises a movable cover for the outlet, wherein the cover:
is movable from an at rest position, in which the cover covers the outlet, to a primed position and then an actuated position to uncover the outlet, and couples to the dispensing mechanism such that: movement of said cover from the primed position to the actuated position actuates one or more components of the dispensing mechanism, and movement of said cover from the at rest position to the primed position does not actuate said one or more components of the dispensing mechanism.

2. A medicament dispenser according to claim 1, wherein the movable cover couples to said release and said at least one indexer for actuation thereof.

3. A medicament dispenser according to claim 1, wherein said movable cover is coupled to the dispensing mechanism by gearing.

4. A medicament dispenser according to claim 1, further comprising a track along which the movable cover is movable from the at rest position, to the primed position and then to the actuated position.

5. A medicament dispenser according to claim 4, wherein the track is on the housing.

6. A medicament dispenser according to claim 1, wherein the movable cover is mounted to the housing for arcuate movement relative thereto from the at rest position, to the primed position and then to the actuated position.

7. A medicament dispenser according to claim 1, wherein the at least one indexer is comprised of an index wheel for each medicament carrier.

8. A medicament dispenser according to claim 1, wherein the release is comprised of a take-up spindle for each medicament carrier.

9. A medicament dispenser according to claim 1 for containing plural blister strip form medicament carriers, each medicament carrier having multiple distinct pockets for containing medicament dose portions, wherein said pockets are spaced along the length of and defined between two peelable sheets secured to each other, said dispensing mechanism comprising,
a) an opening station for receiving a pocket of each of said medicament carriers; and
b) at least one peeler positioned to engage a base sheet and a lid sheet of a pocket which has been received in said opening station for peeling apart such a base sheet and lid sheet, to open such a pocket; and
wherein the outlet is positioned to be in communication with an opened pocket and through which a user can access a medicament dose portion from such an opened pocket; and the at least one indexer is for individually indexing the distinct pockets of each of the plural medicament carriers.

10. A medicament dispenser according to claim 9, wherein for each blister strip the dispensing mechanism comprises a lid take-up spindle for winding up the used lid sheet of the blister strip thereon and an index wheel for indexing the blister strips and wherein the movable cover is coupled to the dispensing mechanism such that movement of the movable cover from the at rest position to the primed position does not result in any rotation of the lid takeup spindles and index wheels, but further movement of the movable cover to the actuated position results in sufficient rotation of the lid take-up spindles and index wheels to advance each blister strip by one pocket distance and the leading pocket thereof to be peeled open and brought into communication with the outlet.

11. A medicament dispenser according to claim 1 containing the plural elongate form medicament carriers.

12. A medicament dispenser according to claim 11, wherein the dose portions of each medicament carrier are in powder form.

13. A medicament dispenser according to claim 1 which is an inhalation device with the outlet in the form of a mouthpiece.

14. A medicament dispenser for containing plural elongate blister strip form medicament carriers, each medicament carrier having multiple distinct medicament dose portions carried in multiple distinct pockets which are spaced along the length of and defined between peelable base and lid sheets secured to each other, said dispenser having a housing, and within said housing a dispensing mechanism for dispensing the distinct medicament dose portions carried by each of said plural medicament carriers, said mechanism comprising,
at least one receiving station for receiving each of the plural medicament carriers;
an opening station for receiving a pocket of each of said medicament carriers;
a release for releasing in combination a distinct medicament dose portion from each of the plural medicament carriers on receipt thereof by said receiving station, comprising:
at least one peeler positioned to engage a base sheet and a lid sheet of a pocket which has been received in said opening station for peeling apart such a base sheet and lid sheet, to open such a pocket;
a lid take-up spindle for each medicament carrier for winding up the lid sheet thereon;
an outlet, positioned to be in communication with the distinct medicament dose portions releasable by said release and through which a user can access a medicament dose portion from an opened pocket; and
an index wheel for each medicament carrier for individually indexing the distinct pockets of each of the plural medicament carriers;
wherein said dispenser further comprises a movable cover that couples to the dispensing mechanism and that is movable from an at rest position, in which the cover covers the outlet, to a primed position and then an actuated position to uncover the outlet, and movement of the movable cover is coupled to the index wheels and lid take-up spindles by gearing that is arranged such that movement of the cover from the at rest position to the primed position does not result in any rotation of the index wheels and lid take-up spindles, but further movement of the cover to the actuated position results in sufficient rotation of the index wheels and lid take-up spindles to advance each medicament carrier by one pocket distance.

15. A medicament dispenser according to claim 14, wherein the dose portions of each medicament carrier are in powder form.

16. A medicament dispenser according to claim 14 which is an inhalation device with the outlet in the form of a mouthpiece.

* * * * *